(12) United States Patent
Segil et al.

(10) Patent No.: US 10,905,570 B2
(45) Date of Patent: Feb. 2, 2021

(54) PROSTHETIC PARTIAL FINGERS

(71) Applicants: The Regents of the University of Colorado, a body corporate, Denver, CO (US); Point Designs LLC, Louisville, CO (US)

(72) Inventors: Jacob Segil, Boulder, CO (US); Stephen Huddle, Thornton, CO (US); Levin Sliker, Erie, CO (US); Richard Weir, Longmont, CO (US)

(73) Assignees: The Regents of the University of Colorado, a body corporate, Denver, CO (US); Point Designs LLC, Louisville, CO (US)

( * ) Notice: Subject to any disclaimer, the term of this patent is extended or adjusted under 35 U.S.C. 154(b) by 0 days.

(21) Appl. No.: 16/688,719

(22) Filed: Nov. 19, 2019

(65) Prior Publication Data

US 2020/0155330 A1 May 21, 2020

Related U.S. Application Data

(60) Provisional application No. 62/769,360, filed on Nov. 19, 2018.

(51) Int. Cl.
*A61F 2/58* (2006.01)
*A61F 2/72* (2006.01)
(Continued)

(52) U.S. Cl.
CPC ............ *A61F 2/586* (2013.01); *A61F 2/5046* (2013.01); *A61F 2/66* (2013.01); *A61F 2/72* (2013.01);
(Continued)

(58) Field of Classification Search
CPC ....................................................... A61F 2/586
See application file for complete search history.

(56) References Cited

U.S. PATENT DOCUMENTS

| 2,669,727 | A | * | 2/1954 | Opuszenski | .............. | A61F 2/58 |
| | | | | | | 623/64 |
| 4,090,264 | A | | 5/1978 | Thompson | | |
| (Continued) | | | | | | |

FOREIGN PATENT DOCUMENTS

EP 2542189 B1 5/2015

OTHER PUBLICATIONS

Naked Prosthetics, "Home," https://www.npdevices.com, 10 pages, Nov. 15, 2019.
(Continued)

*Primary Examiner* — Bruce E Snow
*Assistant Examiner* — Melissa A Hoban
(74) *Attorney, Agent, or Firm* — Brownstein Hyatt Farber Schreck, LLP

(57) ABSTRACT

Various embodiments of the present invention generally relate to prosthetic partial finger designs that can mimic the last two joints of the finger. Some embodiments include a proximal phalange, a distal phalange coupled to the proximal phalange, and a knuckle track (e.g., formed in an arc). The knuckle track can be moveably coupled to the proximal phalange an may include multiple teeth formed on which the proximal phalange slides along. A ratcheting mechanism can contact the multiple teeth to allow sliding in only a first direction while the ratcheting mechanism is engaged. Some embodiments include a release mechanism (e.g., a button) configured to disengage the ratcheting mechanism from the multiple teeth to allow the distal phalange to slide in a second direction. In some embodiments, the device may include a spring-back capability that automatically extends
(Continued)

the finger after reaching full finger flexion, enabling one-handed use.

30 Claims, 16 Drawing Sheets

(51) Int. Cl.
    *A61F 2/66*     (2006.01)
    *A61F 2/50*     (2006.01)
    *B33Y 80/00*     (2015.01)

(52) U.S. Cl.
    CPC ....... *B33Y 80/00* (2014.12); *A61F 2002/5038* (2013.01); *A61F 2002/5056* (2013.01); *A61F 2002/5072* (2013.01); *A61F 2002/587* (2013.01); *A61F 2002/6621* (2013.01)

(56) References Cited

U.S. PATENT DOCUMENTS

| | | | |
|---|---|---|---|
| 4,685,929 A | 8/1987 | Monestier | |
| 5,062,855 A | 11/1991 | Rincoe | |
| 6,908,489 B2 | 6/2005 | Didrick | |
| 8,100,986 B2 | 1/2012 | Puchhammer et al. | |
| 8,177,856 B2 | 5/2012 | Jaworski | |
| 9,072,614 B2 | 7/2015 | Starkey et al. | |
| 9,126,342 B2 | 9/2015 | Birglen | |
| 9,211,200 B2 | 12/2015 | Moyer et al. | |
| 9,370,430 B2 | 6/2016 | Macduff | |
| 9,375,319 B2 | 6/2016 | Macduff | |
| 9,629,731 B2 | 4/2017 | Thompson, Jr. et al. | |
| 9,707,101 B2* | 7/2017 | Thompson, Jr. | A61F 2/586 |
| 9,999,521 B2 | 6/2018 | Thompson, Jr. et al. | |
| 2005/0043822 A1 | 2/2005 | Didrick | |
| 2006/0212129 A1 | 9/2006 | Lake | |
| 2010/0036507 A1 | 2/2010 | Gow | |
| 2012/0146352 A1* | 6/2012 | Haslinger | B25J 9/102 |
| | | | 294/198 |
| 2013/0046395 A1 | 2/2013 | McLeary | |
| 2014/0303741 A1 | 10/2014 | Macduff | |
| 2015/0374515 A1 | 12/2015 | Meijer et al. | |
| 2017/0049583 A1* | 2/2017 | Belter | A61F 2/5046 |
| 2019/0298553 A1 | 10/2019 | Gibbard et al. | |
| 2019/0328550 A1* | 10/2019 | Akhtar | A61F 2/586 |

OTHER PUBLICATIONS

Partial Hand Solutions LLC, "Prosthetic Devices," https://partialhandsolutions.com, 6 pages, Nov. 15, 2019.
Point Designs LLC, "The Point Digit II," 9 pages, Nov. 18, 2019.
Segil, Jacob L. et al., "The Point Digit: Mechanical Design and Testing of a Ratcheting Prosthetic Finger," 41st Annual Meeting of the American Society of Biomechanics, 2 pages, Aug. 8-11, 2017.
ten Kate, Jelle et al., "3D-Printed Upper Limb Prostheses: A Review," Disability and Rehabilitation: Assistive Technology, vol. 12, No. 3, pp. 300-314, Feb. 2, 2017.
Touch Bionics, "i-limb digits Clinician Manual," Issue No. 2, 38 pages, Dec. 2014.
International Application No. PCT/US2019/062228, International Search Report & Written Opinion, 13 pages, dated Mar. 17, 2020.

* cited by examiner

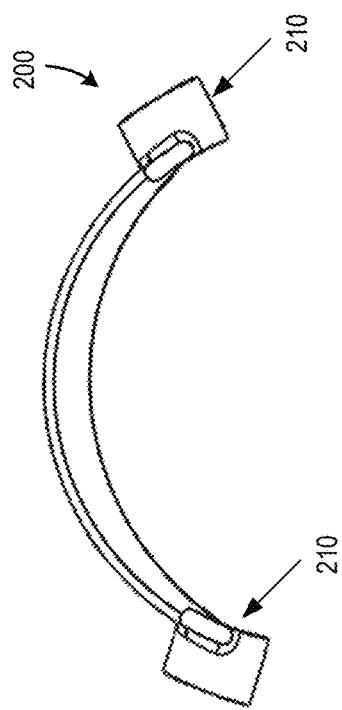
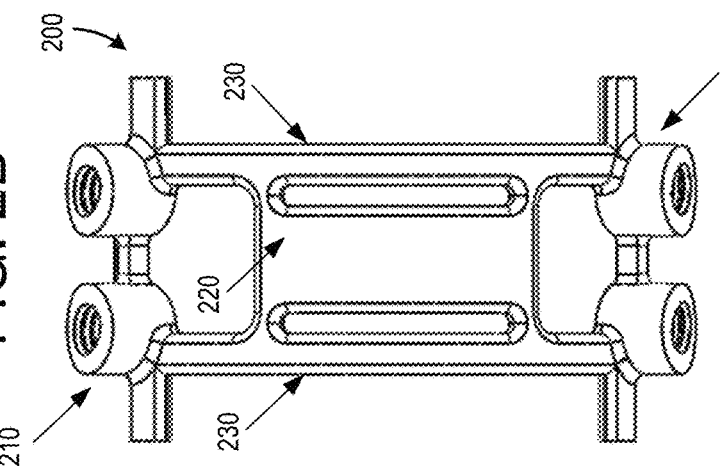
FIG. 2B
FIG. 2C
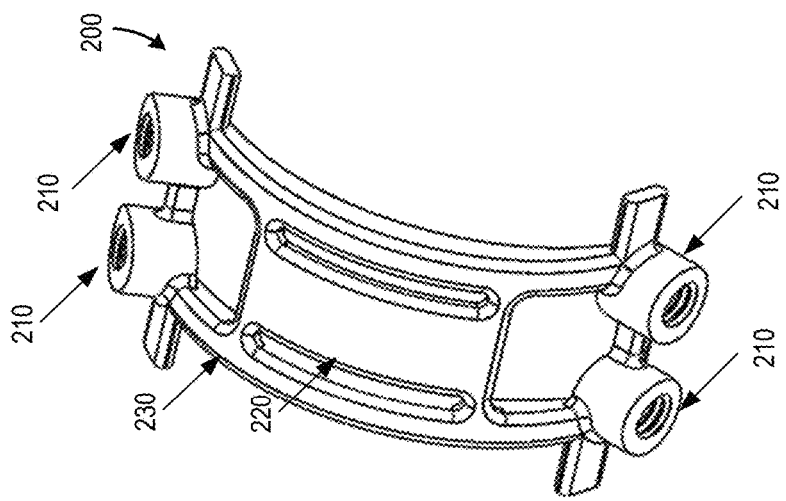
FIG. 2A

PROSTHETIC PARTIAL FINGERS

CROSS-REFERENCE TO RELATED APPLICATIONS

This application claims priority to U.S. Provisional Application Ser. No. 62/769,360 filed Nov. 19, 2018, which is incorporated herein by reference in its entirety for all purposes.

STATEMENT REGARDING FEDERALLY SPONSORED RESEARCH

This invention was made with government support under grant numbers 1 R41 HD096942-01 awarded by the NIH NICHD. The government has certain rights in the invention.

TECHNICAL FIELD

Various embodiments of the present invention generally relate to prosthetic devices. More specifically, some embodiments of the present technology relate to prosthetic partial fingers.

BACKGROUND

There are an estimated 500,000 amputees with partial hand amputations. Various types of prosthetic devices can be used to replace a missing body parts (e.g., a limb, a finger, etc.). The most common upper limb amputation is partial hand amputation with loss of one or more fingers. Some traditional devices are purely cosmetic and provide static limb replacements no movement or functionality. Other devices are body powered with cabling to the wrist joint or palm of the hand. When the wrist or palm of the hand is flexed that will cause the prosthetic device to automatically flex. Moreover, in order to maintain flexion of the finger with these traditional cabled devices, the user must continually flex the wrist or palm. This can be tiring when manual performing tasks that require flexion of the fingers for an extended period of time (e.g., mowing the lawn). Moreover, these traditional devices typically do not create much mechanical advantage and break easily. As such, new prosthetic designs are needed to provide a cost effective set of fingers that provide a robust set of anatomical restorations.

SUMMARY

Various embodiments of the present invention generally relate to prosthetic devices. More specifically, some embodiments of the present technology relate to prosthetic partial fingers. Some embodiments comprise a proximal phalange, a distal phalange coupled to the proximal phalange, and a knuckle track formed in an arc and configured to be moveably coupled to the proximal phalange. In accordance with various embodiments, the proximal phalange, the distal phalange, and the knuckle track, can be made out of different materials (e.g., plastic, metal, etc.). In some embodiments, the knuckle track can include multiple teeth formed on a first side on which the proximal phalange slides along. The proximal phalange can include a ratcheting mechanism to contact the multiple teeth to allow sliding in only a first direction while the ratcheting mechanism is engaged. Some embodiments include release mechanism (e.g., a button) configured to disengage the ratcheting mechanism from the multiple teeth to allow the distal phalange to slide in a second direction. In some embodiments, the distal phalange can be coupled to the proximal phalange using a screw.

Some embodiments provide for method that includes exposing a mounting hole on a mounting bracket after lamination to provide one or more points of attachment. The mounting bracket can capture a knuckle track beneath providing a low-profile installation. One or more extensions of the mounting bracket can be bent to conform the mounting bracket to a socket shape.

Some embodiments provide for a device comprising a knuckle track formed in an arc, a proximal phalange, a distal phalange, and a means for coupling the distal phalange to the proximal phalange. In accordance with some embodiments, the proximal phalange can include a means for moveably coupling the proximal phalange to the knuckle track that allows the proximal phalange to slide in only a first direction until released. In some embodiments, the distal phalange can be coupled to the proximal phalange using a screw.

Some embodiments include a device having a proximal phalange, a distal phalange coupled to the proximal phalange, a knuckle track moveably coupled to the proximal phalange, a ratcheting mechanism to contact multiple teeth to allow sliding in only a first direction while the ratcheting mechanism is engaged, and a release button configured to disengage the ratcheting mechanism from the multiple teeth to allow motion of the distal phalange or proximal phalange.

In some embodiments, a mounting hole can be exposed on a mounting bracket after lamination to provide one or more points of attachment. The mounting bracket can capture a knuckle track beneath providing a low-profile installation. One or more extensions of the mounting bracket can be bent to conform the mounting bracket to a socket shape.

While multiple embodiments are disclosed, still other embodiments of the present technology will become apparent to those skilled in the art from the following detailed description, which shows and describes illustrative embodiments of the technology. As will be realized, the technology is capable of modifications in various aspects, all without departing from the scope of the present technology. Accordingly, the drawings and detailed description are to be regarded as illustrative in nature and not restrictive.

BRIEF DESCRIPTION OF THE DRAWINGS

Embodiments of the present technology will be described and explained through the use of the accompanying drawings.

FIGS. 2A-2C illustrate various views of an example of a mounting bracket for a prosthetic finger system that may be used in accordance with various embodiments of the present technology.

Figure 1A:
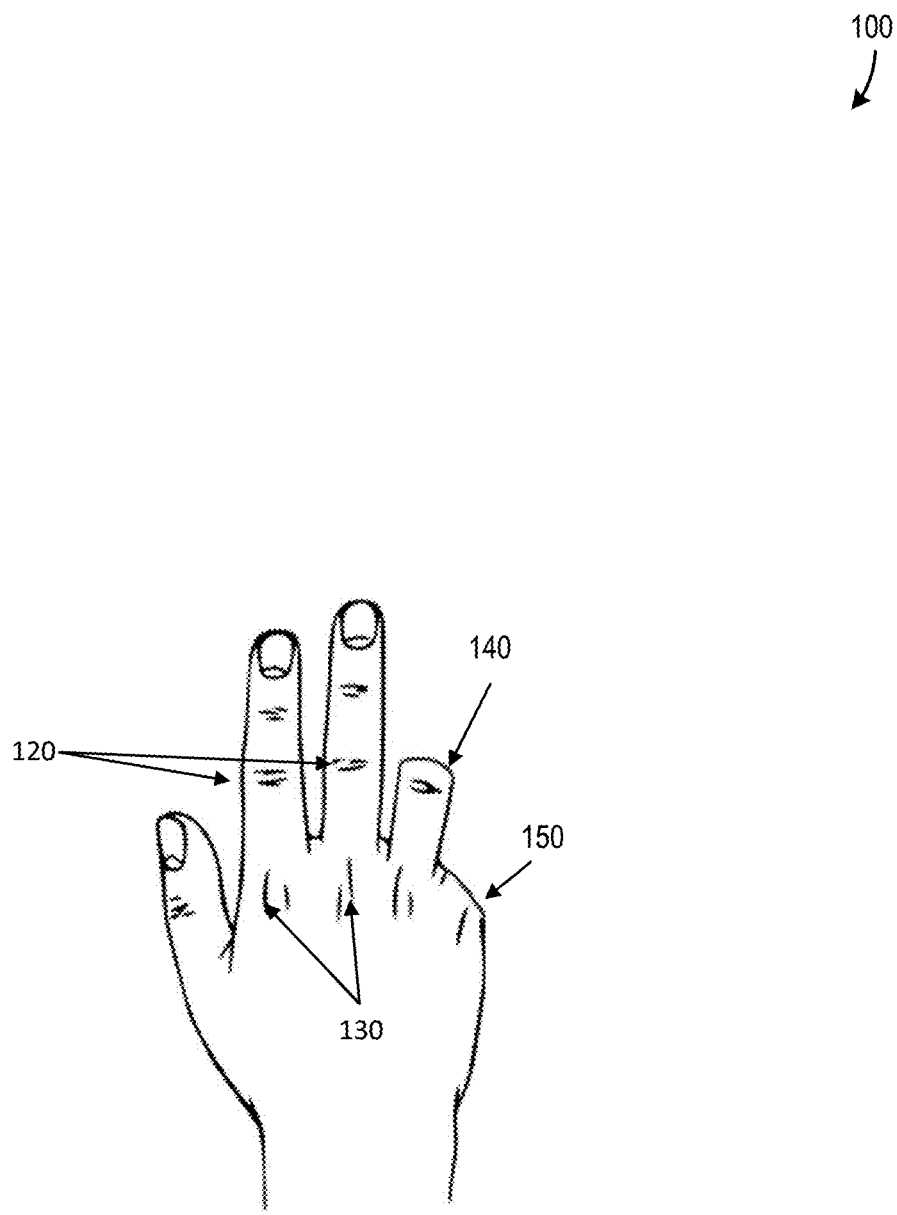
FIG. 1A illustrates an example of a hand with a partial finger amputation in which some embodiments of the present technology may be utilized.

The drawings have not necessarily been drawn to scale. Similarly, some components and/or operations may be separated into different blocks or combined into a single block for the purposes of discussion of some of the embodiments of the present technology. Moreover, while the technology is amenable to various modifications and alternative forms, specific embodiments have been shown by way of example in the drawings and are described in detail below. The intention, however, is not to limit the technology to the particular embodiments described. On the contrary, the technology is intended to cover all modifications, equivalents, and alternatives falling within the scope of the technology as defined by the appended claims.

DETAILED DESCRIPTION

Various embodiments of the present invention generally relate to prosthetic devices. More specifically, some embodiments of the present technology relate to prosthetic partial finger designs. One of the most common upper limb amputations is the partial finger amputation. Individuals with partial finger amputations often retain one or more fingers and the missing limbs often include a residual limb that a prothesis can be mounted onto. Traditional designs are ineffective in allowing the individual to perform manual tasks over longer periods of time (e.g., mowing the lawn, using a hammer, etc.) as these traditional devices are purely cosmetic and do not restore any of the lost functionality or have complex cabling systems which require the individual to maintain a flexed wrist or palm.

In contrast, various embodiments of the present technology provide a partial finger device that can mimic the last two joints of the finger. Some embodiments use a passive design without any cabling but instead include a ratcheting mechanism that allows the individual to position the device independent of the posture of the residual limb. Upon completion a release button can be engaged to release the ratcheting mechanism and allow the finger to be extended. In some embodiments, the ratcheting mechanism provides multiple distinct amounts of finger flexion (e.g., five states, ten states, fifteen states, etc.). In some embodiments, the device may include a spring-back capability that automatically extends the finger after reaching full finger flexion, enabling one-handed use. A mounting track can be used in some embodiments to provide a center of rotation about the physiological joint recreating the physiological kinematics. Some embodiments can use of a metal laser sintering 3D printer to manufacture the components allows for unique mechanical designs to provide high strength at a low weight. The fingers can be scaled to larger or smaller hand sizes and customized to match the physiological hand.

Some embodiments of the present technology provide a non-powered ratcheting mechanical prosthetic partial finger. A mounting kit can contain everything needed for a trained prosthetist to install one (1) to four (4) point partial(s) into a prosthetic socket, including mounting brackets, alignment/lamination tools, and mounting screws. The mounting bracket used in some embodiments can provide an attachment point between the prosthetic socket and the prosthetic finger. Two mounting brackets may be used for each prosthetic finger device in some embodiments. The mounting bracket can be aligned on the socket and laminated into the socket by a trained prosthetist or technician. Using the mounting screws, lamination spacers can be attached to the mounting bracket during the lamination process in place of some embodiments of the prosthetic fingers to maintain the mounting location. After lamination, the prosthetic digit can be attached to the mounting bracket using the mounting screws.

Various embodiments of the present technology provide for a wide range of technical effects, advantages, and/or improvements to computing systems and components. For example, various embodiments include one or more of the following technical effects, advantages, and/or improvements: 1) prosthetic partial finger that is durable and can withstand high loads; 2) integrated use of three-dimensional printing to fabricate complex mechanical prosthetic devices that can be automatically scaled; 3) unique spherical ratcheting mechanism allowing for prolonged flexion without continued effort on behalf of the user; 4) use of unconventional and non-routine computer operations to automatically scale point pivot system design to match the size of the physiological hand; 5) mounting track provides a center of rotation about the physiological joint recreating the physiological kinematics; 6) push button allows for the finger design to be extended when engaged; and/or 7) unique manufacturing processes to handle complex system integration.

In the following description, for the purposes of explanation, numerous specific details are set forth in order to provide a thorough understanding of embodiments of the present technology. It will be apparent, however, to one skilled in the art that embodiments of the present technology may be practiced without some of these specific details. While, for convenience, embodiments of the present technology are described with reference to single independent ratcheting prosthetic finger, other embodiments can use a cable to flex the finger instead of external objects which are necessary with the original design.

For example, the cable could be anchored to the amputee and wrist flexion would cause the cable to pull tension and flex the finger. As another example, some embodiments can provide a coupled prosthetic finger arrangement. As such, a fixture can be installed between prosthetic fingers so that the flexion of one finger causes flexion (potentially at varying degrees) across all other fingers. Still yet, some embodiments can provide for a prosthetic thumb. In some of these embodiments, a prosthetic thumb can have phalange lengths and geometries adjusted to fit the form of a thumb. However, the ratcheting technology could still be used. As another example, some embodiments can be used for pediatric and/or women sized digits. Women and children are underserved populations in upper limb prosthetics since most devices are too large. By using the design of the prosthetic finger, and the custom scaling techniques, various embodiments allow for the creation of a smaller version for patients with smaller intact anatomy.

The phrases "in some embodiments," "according to some embodiments," "in the embodiments shown," "in other embodiments," and the like generally mean the particular feature, structure, or characteristic following the phrase is included in at least one implementation of the present technology, and may be included in more than one implementation. In addition, such phrases do not necessarily refer to the same embodiments or different embodiments.

Figure 1B:
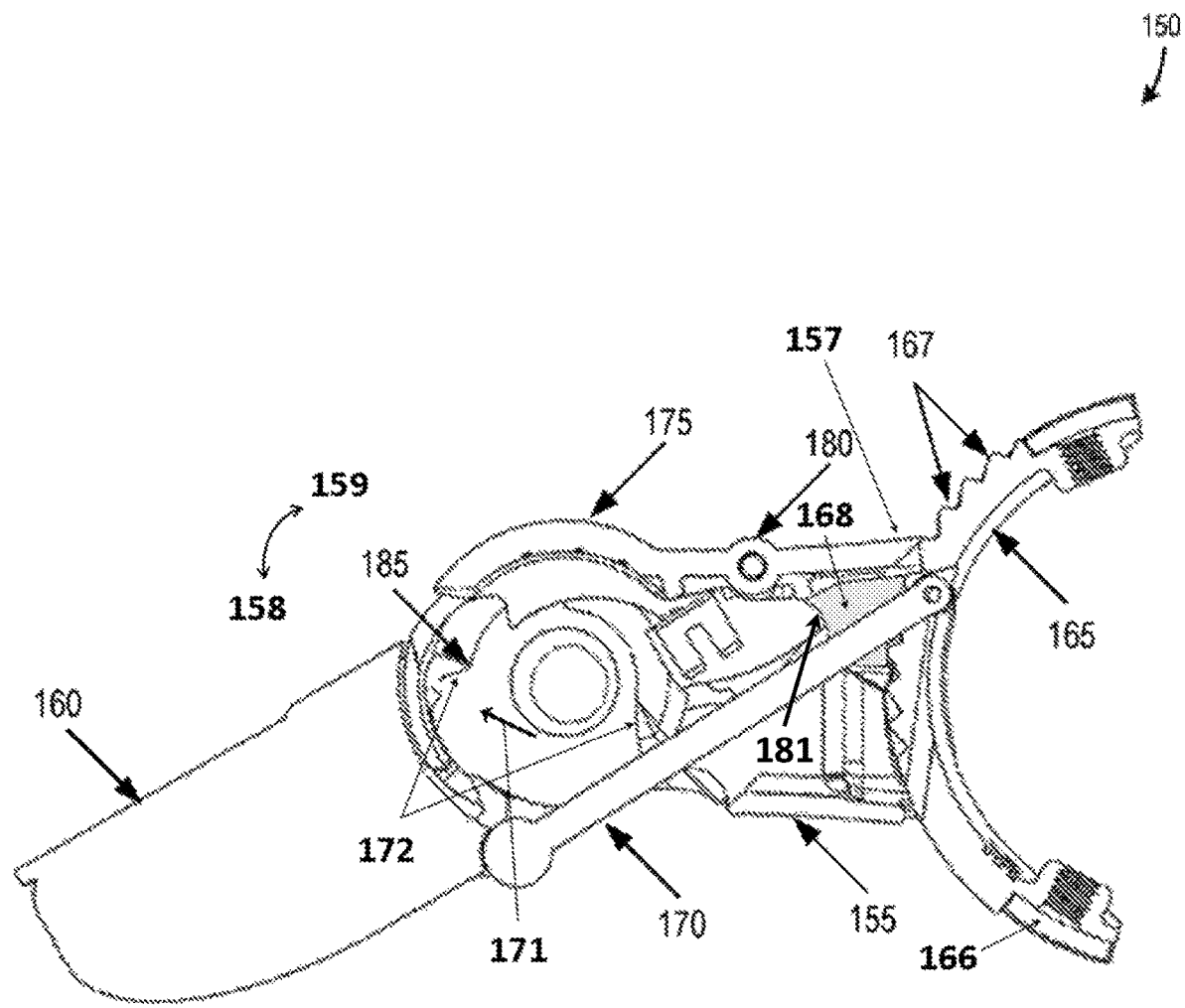
FIG. 1B is a cross-sectional view of an example of a prosthetic device according to one or more embodiments of the present technology.

FIG. 1A illustrates an example of a hand 100 with a partial finger amputation in which some embodiments of the present technology may be utilized. As illustrated in hand 100, FIG. 1B illustrates an example of a prosthetic finger prosthetic device according to one or more embodiments of the present technology. In accordance with various embodiments, a partial finger (or multiple partial finger) prosthetic device can serve people with amputation(s) (e.g., 110 and 120) between the metacarpophalangeal (MCP) joint 130 and the proximal interphalangeal (PIP) joint 140 on the index, middle, ring, and/or little fingers as illustrated in FIG. 1A. Some embodiments provide anatomical flexion and rotation around the PIP joint 140. Some embodiments of the prosthetic finger system include the finger prosthesis and mounting brackets (FIG. 2).

FIG. 1B is a cross-sectional view of an example of a prosthetic device 150 according to one or more embodiments of the present technology. Prosthetic finger design 150 illustrated in FIG. 1B can serve people with amputation between the metacarpophalangeal (MCP) joint 130 and the proximal interphalangeal (PIP) joint 140 as described in FIG. 1A. As illustrated in FIG. 1B, some embodiments can include a proximal phalange 155, a distal phalange 160 coupled to the proximal phalange 155, and a knuckle track 165 formed in an arc to allow for placement around residual portion of a finger. The knuckle track 165 can be configured to be moveably coupled to the proximal phalange 155. In some embodiments, knuckle track 165 and proximal phalange 155 can move relative through each other through a sliding joint, pin joint, or the like. In some embodiments, the distal phalange 160 can be coupled to the proximal phalange 15 using a screw, pin, or other component.

In accordance with various embodiments, the proximal phalange 155, the distal phalange 160, and the knuckle track 165, can be made out of different materials (e.g., plastic, metal, etc.). In some embodiments, the knuckle track 165 can include multiple teeth 167 formed on a first side on which the proximal phalange 155 slides along. The prosthetic device 150 can also include a link bar 170 (or a link chain) connecting the distal phalange 160 to the curved knuckle track 165. The link bar 170 can cause the distal phalange 160 to move relative to both the proximal phalange 155 and the knuckle track 165 as the proximal phalange 155 moves relative to the knuckle track 165. The proximal phalange 155 can include a ratcheting mechanism 157 to contact the multiple teeth 167 to allow sliding in only a first direction 158 while the ratcheting mechanism 157 is engaged. Some embodiments include release mechanism (e.g., a release button 175) configured to disengage the ratcheting mechanism 157 from the multiple teeth 167 to allow the distal phalange 160 to slide in a second direction 159.

In the embodiment illustrated in FIG. 1B, release mechanism 175 may include a linkage to a fixed pivot point 180 so that upon engagement of the release mechanism, the opposite end of the linkage is lifted allowing the proximal phalange 155 to slide in any direction on the knuckle track 165 without engaging the multiple teeth 167. In some embodiments, an elastic restoring force 171 may move the partial finger in a second direction 159 relative to the knuckle track 165 resulting in extension of the partial finger 173 when the release mechanism 175 is activated. Some embodiments of the knuckle track 165 may include protruding stops 166 also shown in FIGS. 4A and 4B) that disengage the release button 175 from the ratcheting mechanism 157 allowing an elastic restoring force 171 (e.g., a torsion spring 172 located in the interface 185 between the distal phalange 160 and the proximal phalange 155) to move the partial finger in the second direction 159 without effort from the user.

Figure 1C:
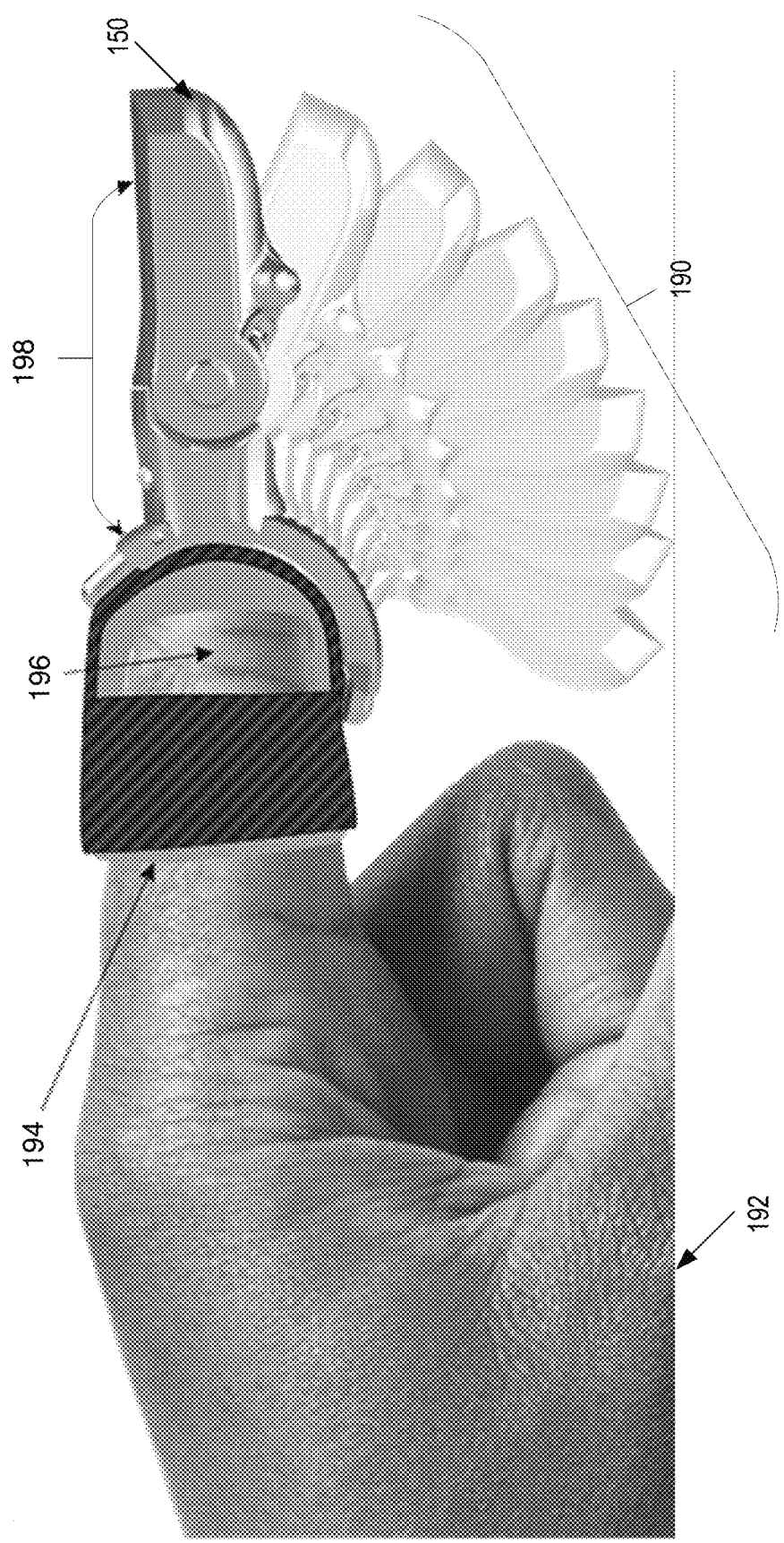
FIG. 1C illustrates an example of the range of motion of a prosthetic device secured to a hand with a silicone and hard shell prosthetic socket to a partial finger amputation.

FIG. 1C illustrates an example of the range of motion 190 of a prosthetic finger prosthetic device 150 secured to a hand 192 with a partial point finger amputation. As illustrated in FIGS. 1B and 1C, the prosthetic finger device 150 can provide a passive functional mechanically articulating prosthetic device for people with 1-4 partial finger (e.g., index, middle, ring, little) amputation(s) between the metacarpophalangeal (MCP) joints and the proximal interphalangeal (PIP) joints. (see, e.g., FIG. 1A and FIG. 1B) The knuckle track can be positioned on a prosthetic socket 194 to allow for a PIP center of rotation 196. The length 198 of the prosthetic finger device 150 can be customized along with other dimensions (e.g., radius and sub-lengths of the distal and proximal phalanges) for differing limb sizes (e.g., that of a child or size of an individual).

FIGS. 2A-2C illustrate various views of an example of a mounting bracket for a prosthetic finger system that may be used in accordance with various embodiments of the present technology. In accordance with various embodiments, one (1) to four (4) prosthetic partial fingers 150, can be installed onto a mounting system. In some embodiments, the mounting system can include: 1) two (2) mounting brackets (see, e.g., FIGS. 2A-2C) for integrating each prosthetic finger device into a prosthetic socket 194 in FIG. 1C (e.g., silicone and hard shell socket fabricated by a certified prosthetist or technician); 2) one (1) to four (4) lamination spacers (equal to the number of prosthetic finger devices); and 3) two (2) to eight (8) mounting screws (e.g., two (2) per prosthetic finger device).

Some embodiments of the prosthetic device can include (or consist only of) a custom prosthetic socket (e.g., 194 in FIG. 1C) and the terminal device. The custom prosthetic socket can be generally fabricated by a certified prosthetist or technician, and may consists of a soft inner liner (e.g., silicone), and a hard outer shell (e.g., carbon fiber). In some embodiments, the terminal device can be a prosthetic partial finger (see, e.g., 150 in FIGS. 1B-1C). The bridge between the terminal device (e.g., prosthetic finger) and the prosthetic socket can be the mounting bracket 200 as illustrated in FIGS. 2A-2C. The mounting bracket 200 may be integrated into the prosthetic socket by way of lamination in some embodiments. As such, only a mounting point 210 may be exposed (FIG. 2A). The mounting point can be used to fix the prosthetic device to the prosthetic socket.

In accordance with various embodiments, mounting bracket 200 may include on or more lattice structures 220 (e.g., made of metal) to create a foundation allowing socket material to adhere. The one or more lattice structures 220 can be connected in an anatomical alignment via linking members 230. The mounting points 210 may be threaded mounting holes that can be used to affix the multiple metal lattice structure to a prosthetic finger. In some embodiments, mounting bracket 200 may include a mounting tab which can be conformed to a shape of a socket and provide additional structural support for the multiple metal lattice structures.

Figure 3A:
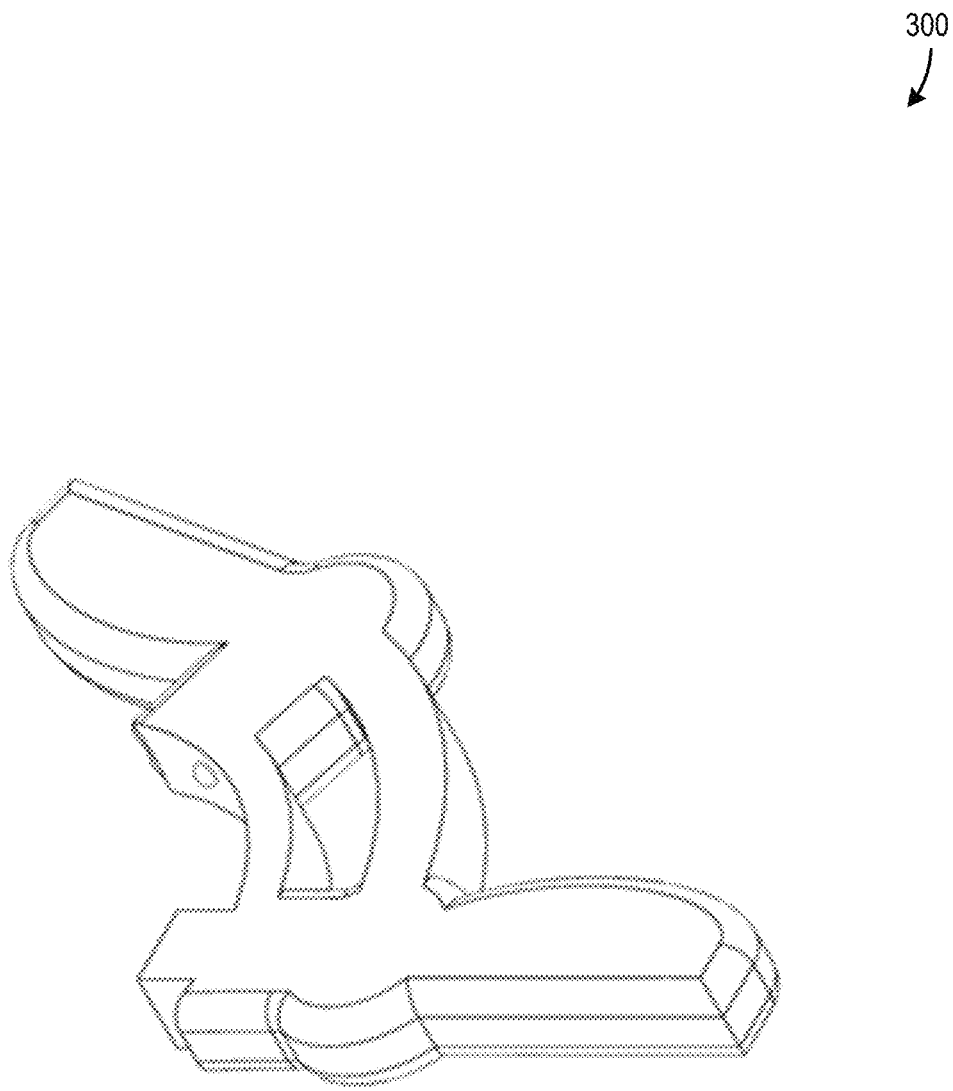
FIG. 3A illustrates an alignment guide that may be used in accordance with one or more embodiments of the present technology.
Figure 3B:
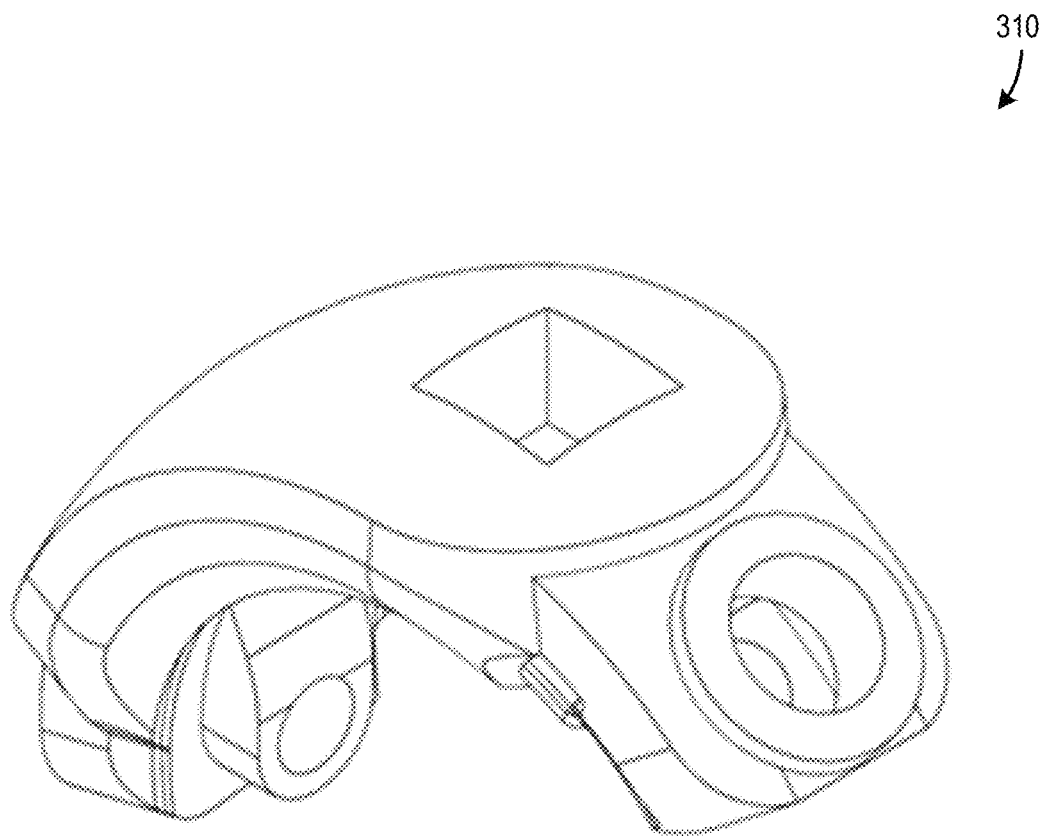
FIG. 3B illustrates an example of a lamination dummy that may be used in accordance with some embodiments of the present technology.
Figure 3C:
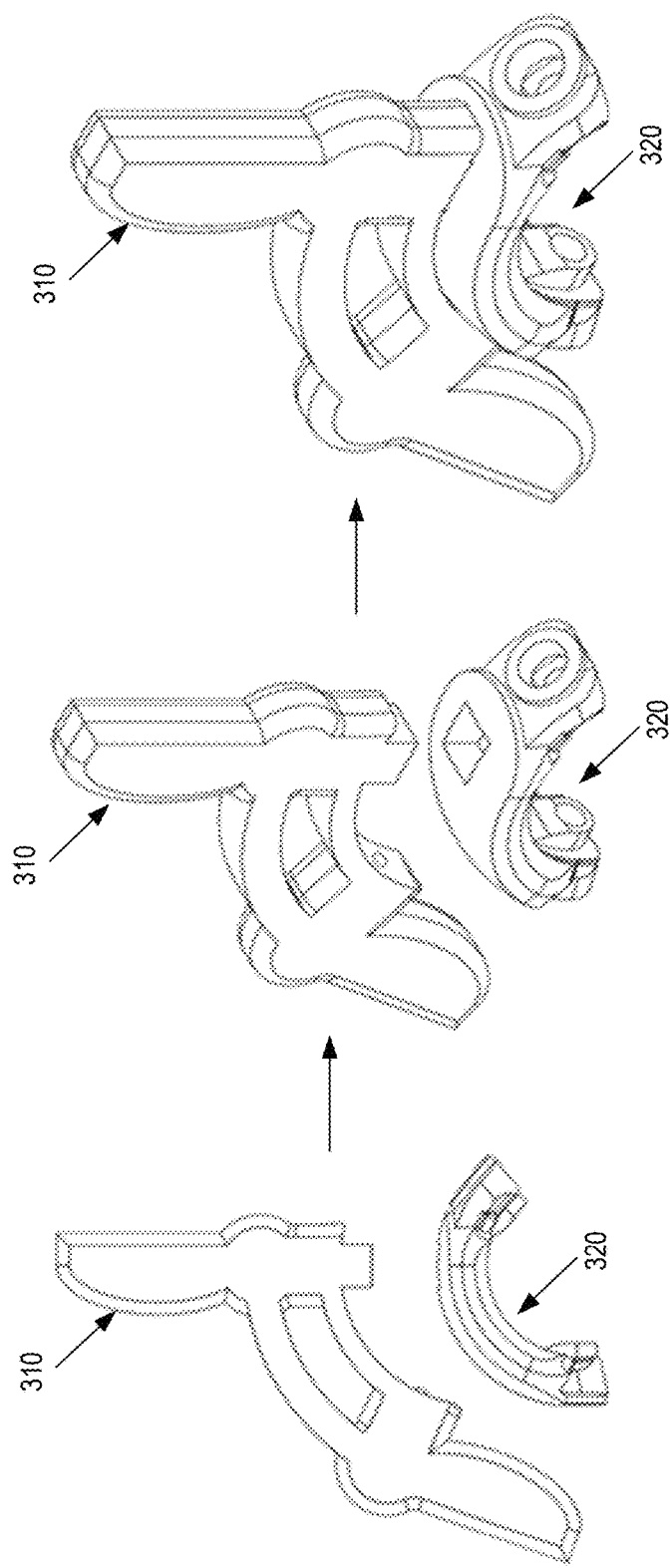
FIG. 3C illustrates how the alignment guide and lamination dummy in FIGS. 3A-3B can connect in accordance with some embodiments of the present technology.

FIG. 3A illustrates an alignment guide 300 that may be used in accordance with one or more embodiments of the present technology. FIG. 3B illustrates an example of a lamination dummy 310 (or lamination tool) that may be used in accordance with some embodiments of the present technology. The alignment guide 300 and lamination tool 320 that can be attached to brackets that may be used in accordance with one or more embodiments of the present technology. In some embodiments, the brackets may be bent to conform to a prosthetic socket (e.g., fabricated by certified prosthetist or technician), and the assembly can be tacked (or otherwise secured) to the socket prior to lamination. The lamination dummy 310 can create a void in a finished socket to allow mounting of a partial finger prosthetic device. The alignment tool 320 can be attached to the lamination dummy as illustrated in the sequence shown in FIG. 3C. The alignment tool mimics a full range of motion a prosthetic partial finger prosthetic device in a plane of motion when in use by a patient.

Fitting Process

Various embodiments of the prosthetic finger system can be compatible with most prosthetic sockets and installed into the prosthetic socket by a trained prosthetist or technician. The mounting bracket can be integrated into a custom prosthetic socket through the following steps; 1) alignment, 2) lamination, and 3) device installation.

Alignment can be performed using the alignment/lamination tool to align the bracket appropriately on the socket. Two (2) brackets can be attached to the alignment tool using the mounting screws. The alignment tool/bracket assembly can then be optimally positioned by the prosthetist on the socket. The bracket tabs can be bent to conform to the socket shape, and then the mounting brackets are tacked onto the socket using medical grade adhesive.

During the lamination process, socket material can be added to the assembly to embed the mounting bracket tabs into the socket. The alignment/lamination tool can be left in place during lamination to maintain the mounting location for each prosthetic finger. The tool prevents any socket material or resin from obstructing the prosthetic finger mounting space. After lamination, the alignment/lamination tool can be removed, and each prosthetic finger can be bolted onto the mounting bracket using two (2) mounting screws in some embodiments.

The following features of various embodiments of the prosthetic finger mounting bracket provide several competitive advantages over other technologies:

1) Exposed mounting hole. In accordance with various embodiments, the mounting hole on the mounting bracket can be exposed after lamination, providing an easy point of attachment for the prosthetic finger. Attachment points for competing technologies are inside the socket, which complicates installation.
2) Bracket location. In some embodiments, the mounting bracket captures the prosthetic finger knuckle track beneath it, providing a low-profile installation. In contrast, the mounting brackets of competing technologies lie underneath the terminal device, increasing build height.
3) Thin bracket profile. In some embodiments, the mounting bracket can be made of stainless steel and may have an optimized thickness to provide enough stability for the prosthetic finger device while maintaining enough malleability to easily bend it to conform to the socket shape. The thin bracket also enables a low-profile installation.
4) Relief holes. In some embodiments, holes can be strategically placed throughout the mounting bracket tabs to promote bonding during lamination for added strength, and to facilitate malleability during alignment prior to lamination.

Figure 4A:
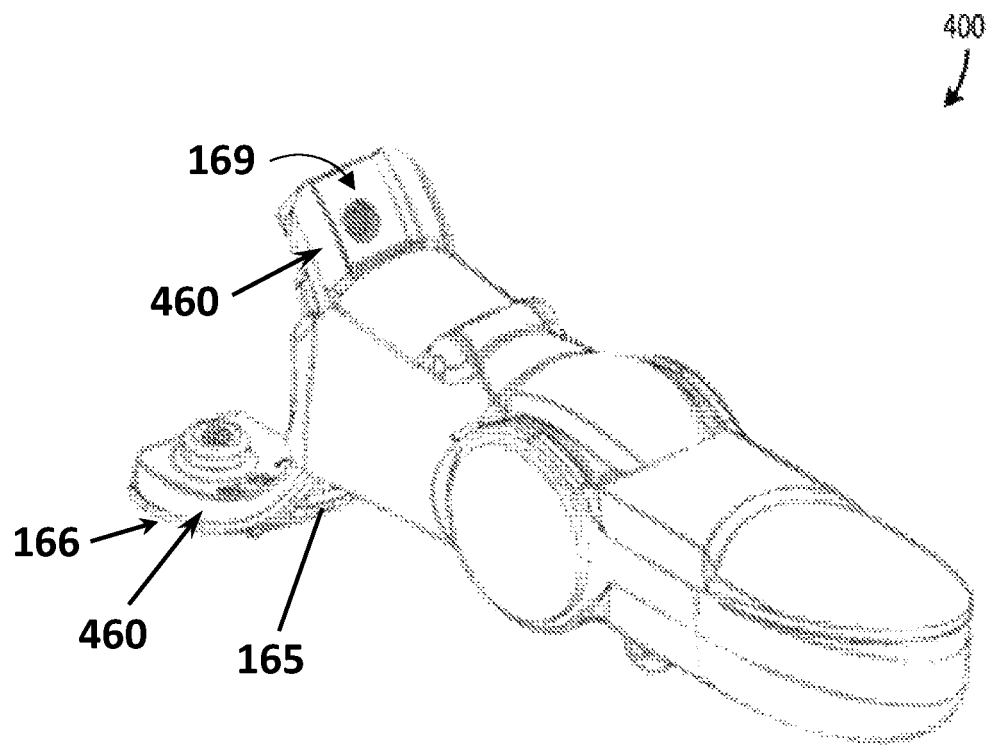
FIGS. 4A-4B illustrates a partial prosthetic device in an extended and flexed position according to one or more embodiments of the present technology.
Figure 4B:
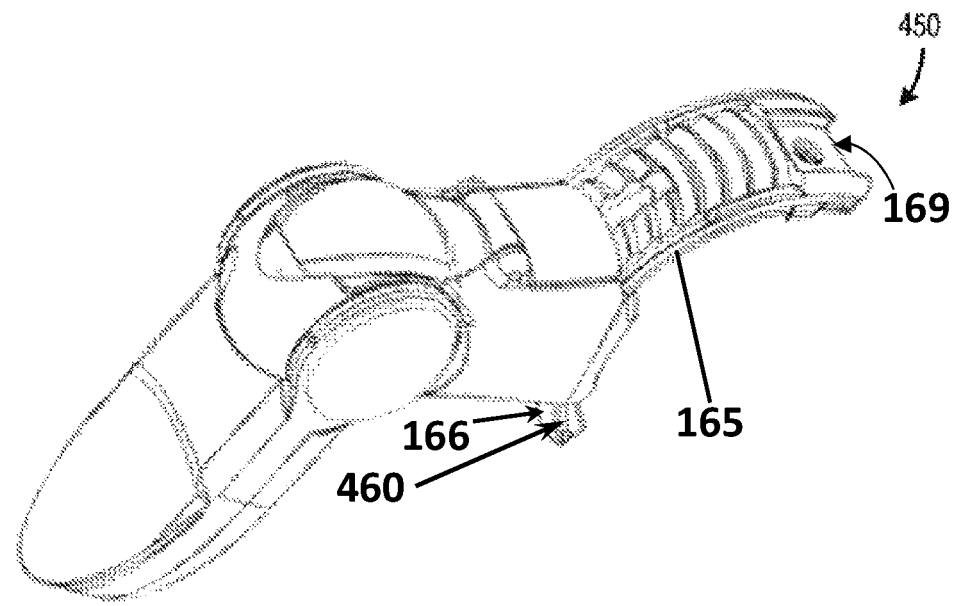
Figure 5A:
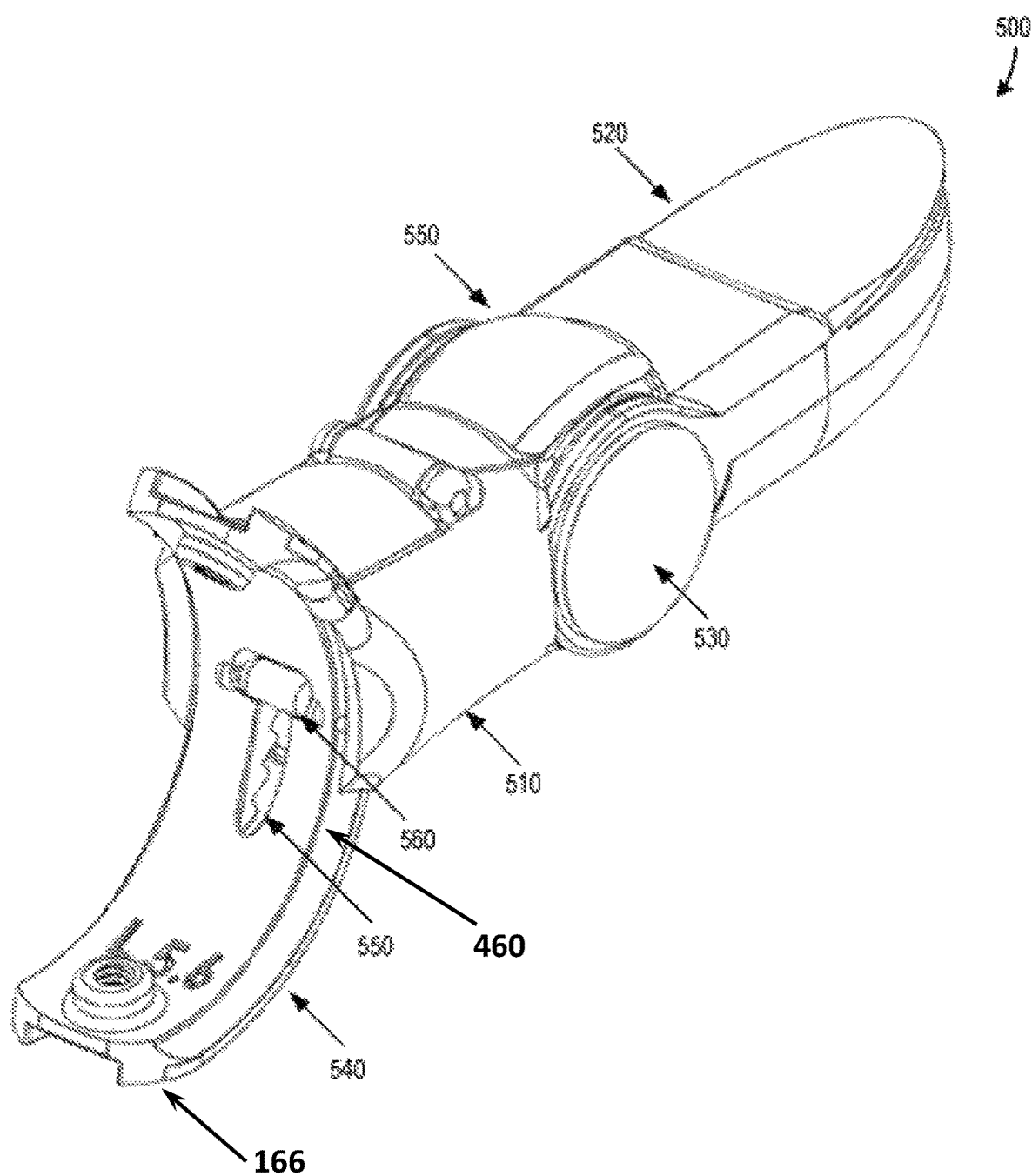
FIGS. 5A-5D illustrate various views of an assembled partial system in accordance with some embodiments of the present technology.
Figure 5B:
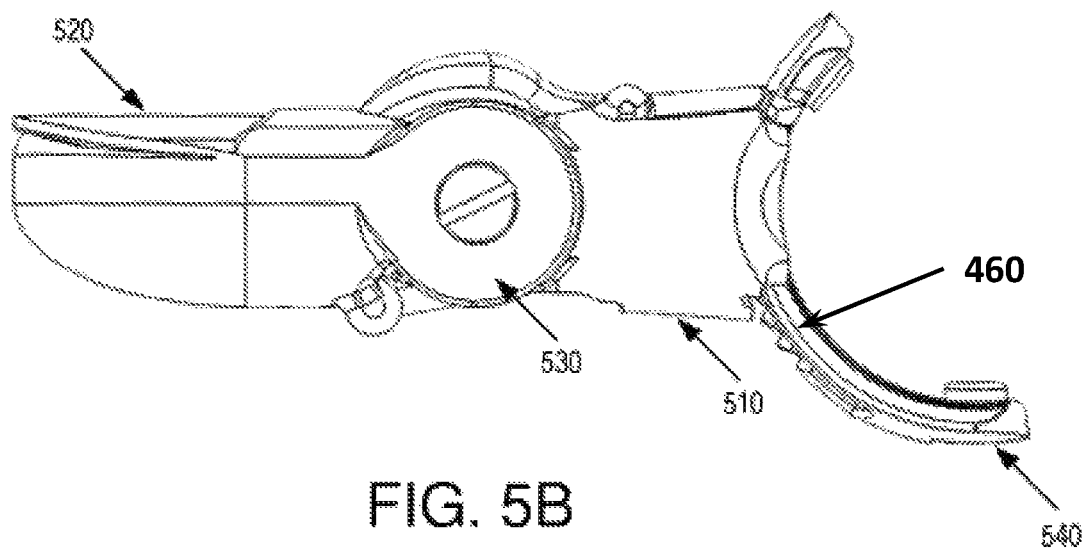
Figure 5C:
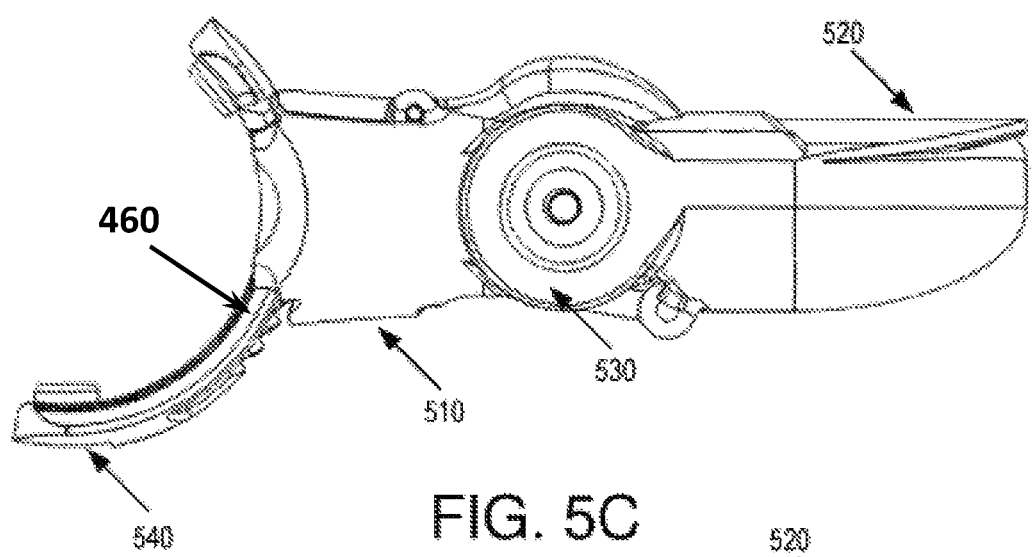
Figure 5D:
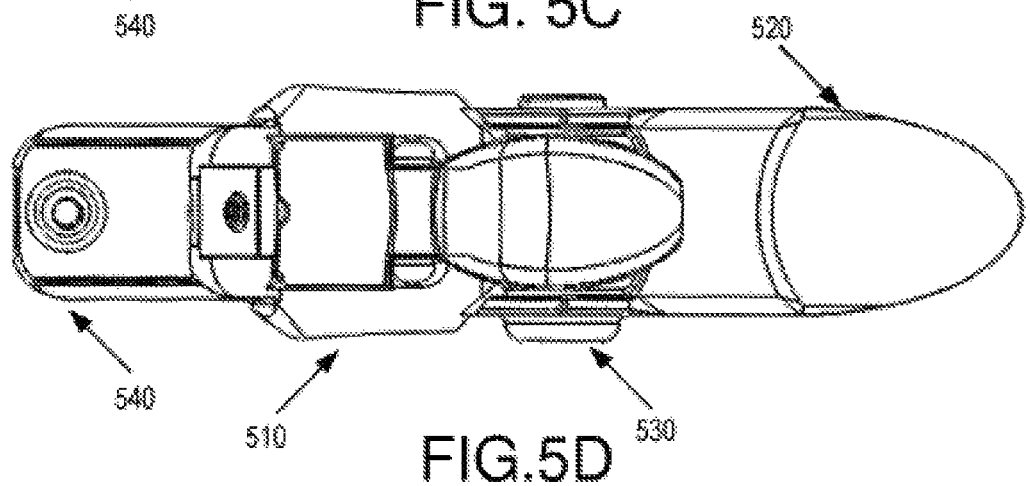

FIGS. 4A-4B illustrates a partial prosthetic device in an extended 400 and flexed 450 position according to one or more embodiments of the present technology. In accordance with various embodiments, the ratcheting mechanism provides multiple (e.g., ten) distinct amounts of finger flexion. The push button can allow for the finger to be extended when engaged. A spring-back capability, present in some embodiments, can extend the finger after reaching full finger flexion, enabling one-handed use. The mounting track 460 can provide a center of rotation about the physiological joint recreating the physiological kinematics. In some embodiments, a metal laser sintering 3D printer (see, e.g., FIG. 10) can be used to manufacture the components allows for unique mechanical designs to provide high strength at a low weight. The fingers can also be scaled to larger or smaller hand sizes and customized to match the physiological hand.

FIGS. 5A-5D illustrate various views of an assembled partial system 500 in accordance with some embodiments of the present technology. In the embodiments illustrated in FIGS. 5A-5D, the assembled partial system 500 can include a proximal phalange 510, a distal phalange 520 coupled to the proximal phalange 510 creating a joint 530, and a curved knuckle track 540 moveably coupled to the proximal phalange 510. In some embodiments, the curved knuckle track, the proximal phalange, and the distal phalange include a ratcheting mechanism to contact multiple teeth to allow movement in only a first direction while the ratcheting mechanism is engaged. A release button (e.g., 175, shown in FIG. 1B), when engaged, disengages the ratcheting mechanism from the multiple teeth allowing a load from a spring (or other elastic restorative force) to move the proximal phalange 510 or the distal phalange 520 in a second direction.

In some embodiments, curved knuckle track 540 can include an aperture 550 allow for connection of one end of a linking bar or chain 560. As illustrated in FIGS. 5A-5D, the linking bar or chain 560 may be positioned internally to the assembled partial system 500 connecting the curved knuckle track to the distal phalange 520 causing flexion of the distal phalange 520 relative to the proximal phalange 510 via joint 530. Some embodiments can include props 168 also shown in FIG. 1B), when engaged, disengage the release button from the ratcheting mechanism allowing a load from a spring to move the proximal phalange or the distal phalange in the second direction. The curved knuckle track 540 can includes a channel 169 (e.g., as shown in FIGS. 4A and 4B) on lateral edges of a first side to allow the props 168 to engage. In some embodiments, the curved knuckle track 540 can have protruding stops at a first end corresponding to full flexion of a finger created by the proximal phalange 510 and the distal phalange 520. The protruding stops may be adjustable or moveable along the curved knuckle track 540 resulting in a change in the full flexion of the finger created by the proximal phalange 510 and the distal phalange 520. In some embodiments, the proximal phalange reaches full flexion at the end of the curved knuckle track and activates a full flexion spring release point to disengage the ratcheting mechanism.

Figure 6:
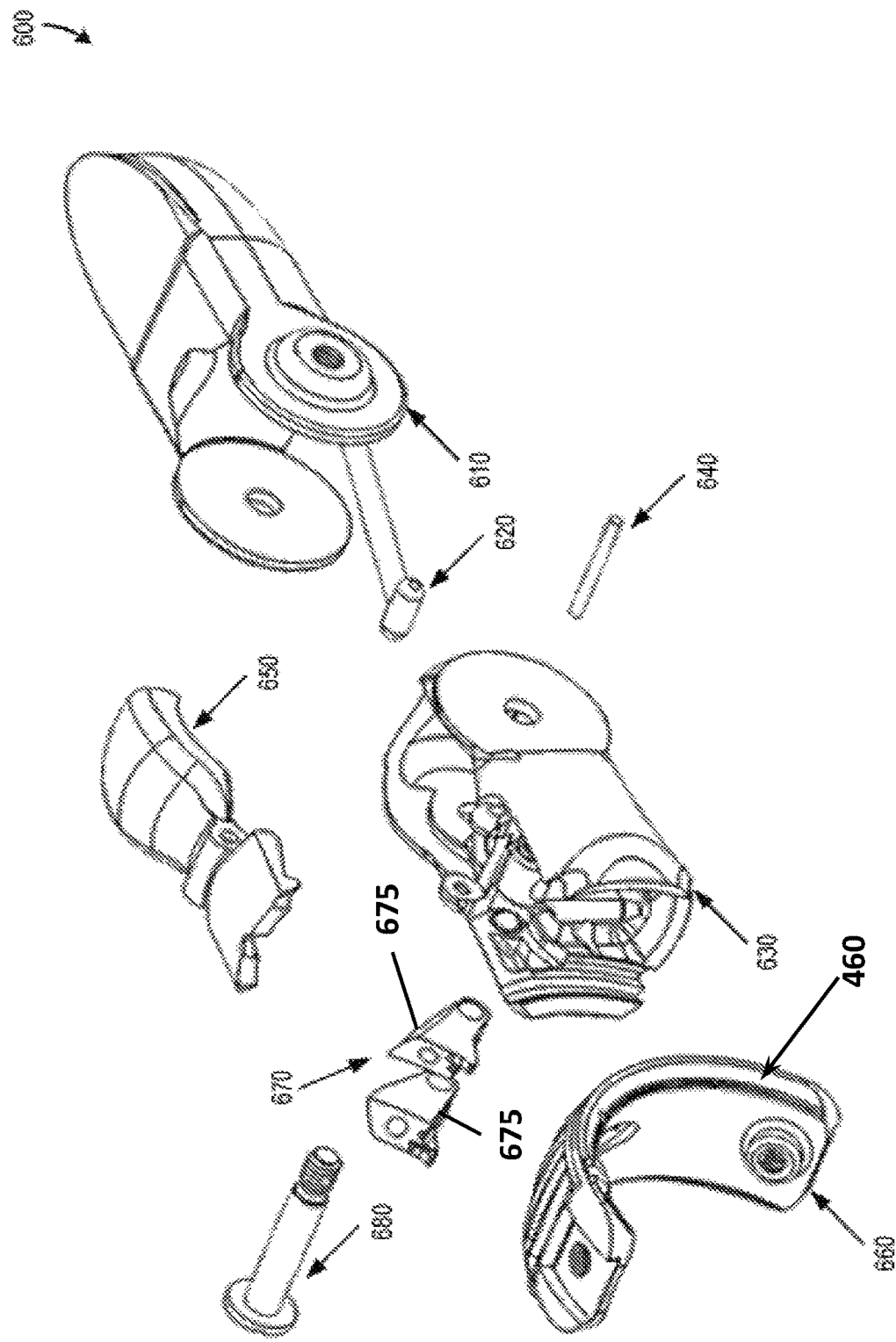
FIG. 6 illustrates an exploded view of a partial finger system illustrating various component that may be present in accordance with one or more embodiments of the present technology.
Figure 7B:
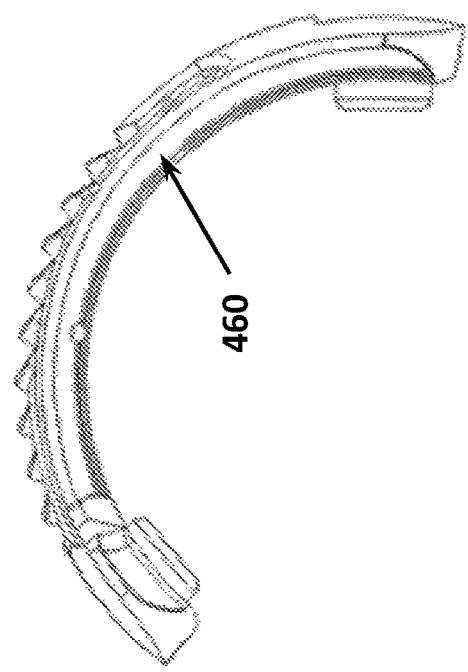
FIGS. 7A-7C illustrate various views of a knuckle track that may be used in various embodiments of the present technology.
Figure 7C:
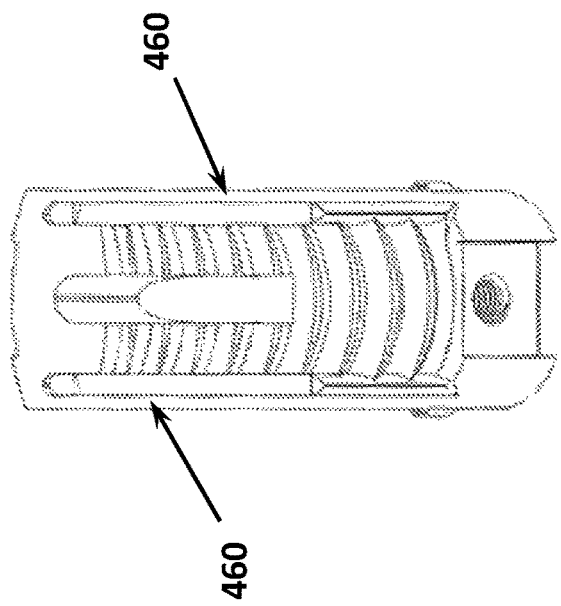
Figure 7A:
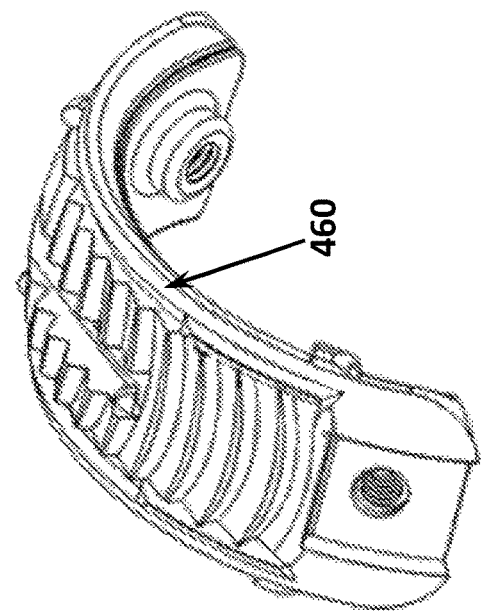

FIG. 6 illustrates an exploded view 600 of a partial finger system illustrating various component that may be present in accordance with one or more embodiments of the present technology. As illustrated in FIG. 6, some embodiments of the partial finger system may include a distal phalange 610, a connecting rod 620, a proximal phalange 630, link bar 640, a release mechanism 650, knuckle track 660, ratcheting mechanism 670, and a screw 680. The distal phalange 610 can be coupled to the proximal phalange 630 using screw 680 (or other coupling member). The knuckle track 660 can be formed in an arc and configured to be coupled to the proximal phalange 630 via rails or bars alongside the knuckle track 660. FIGS. 7A-7C illustrate various views of a knuckle track 660 that may be used in various embodiments of the present technology.

The knuckle track can include multiple teeth formed on a first side on which the proximal phalange 630 slides along. The ratcheting mechanism 670 can contact the multiple teeth to allow sliding in only a first direction while the ratcheting mechanism is engaged. The release button 650 can coupled to the proximal phalange 630 using bar 640. Release button 650 when pressed can rotate around a pivot point created by bar 640 and disengage the ratcheting mechanism from the multiple teeth (e.g., at least five, ten, fifteen, or more) to allow the distal phalange 610 and/or proximal phalange 630 to slide in a second direction.

In some embodiments, the knuckle track 660 rounds in a lateral direction and a transverse direction relative to the multiple teeth so that the arc forms a sector of a sphere. The distal phalange 610, the knuckle track 660, and the release button 650 may all be printed using additive manufacturing techniques and systems (e.g., a three-dimensional printer). In some embodiments, a design tool may automatically scale (e.g., by a computer system) dimensions of the device based on a parameterized model of the device and wherein the computer system controls the three-dimensional printer to print the device in accordance with the dimensions. The link bar 640 and distal phalange 610 can be three-dimensionally printed assembled with a live-hinge in some embodiments. One or more props 675 and the proximal phalange 630 may be printed by a three-dimensional printer assembled with a live-hinge (e.g., live-hinge 181, as shown in FIG. 1B). The proximal phalange 630 and the distal phalange 610 may be shaped in a form of a finger, thumb, or a toe. In addition, in some embodiments, partial finger system may include a ridge simulating a fingernail on the distal phalange 610.

The connecting rod 620 can have a proximal end and a distal end. The proximal end can be affixed to the knuckle track 660 and the distal end is affixed to the distal phalange 610. For example, in some embodiments, the proximal phalange 630 may include an opening through which the connecting rod 620 is positioned. As the proximal phalange 630 is slides along the knuckle track 660 in the first direction, the connecting rod 620 causes the distal phalange 610 to flex relative to the proximal phalange 660.

In some embodiments, a mounting bracket having one or more pliable extensions that can be bent to conform the mounting bracket to a socket can be configured to fit over a remaining portion of a finger and wherein the mounting bracket is securely affixed to a socket using one or more connecting mechanisms. The mounting bracket includes can include relief holes to promote bonding during lamination and exposed mounting holes for ease of attachment. The mounting bracket may be detachable an include multiple lattice structures threaded mounting holes and a mounting tab (see, e.g., FIG. 8). The multiple metal lattice structures can create a foundation allowing socket material to adhere. In some embodiments, the multiple metal lattice structures can be connected in an anatomical alignment via linking members. The threaded mounting holes can affix the multiple metal lattice structure to a prosthetic finger. The mounting tab, which can be conformed to a shape of the socket, can provide additional structural support for the multiple metal lattice structures.

While not illustrated in FIG. 6, in some embodiments, the device can include a cable connected to a wrist attachment or a palm attachment that engages the release button upon flexion of a wrist or palm by a user to activate the wrist attachment or the palm attachment. In some embodiments, electronics providing myoelectric control of the device to cause flexion or extension in response to muscular contractions.

Figure 8:
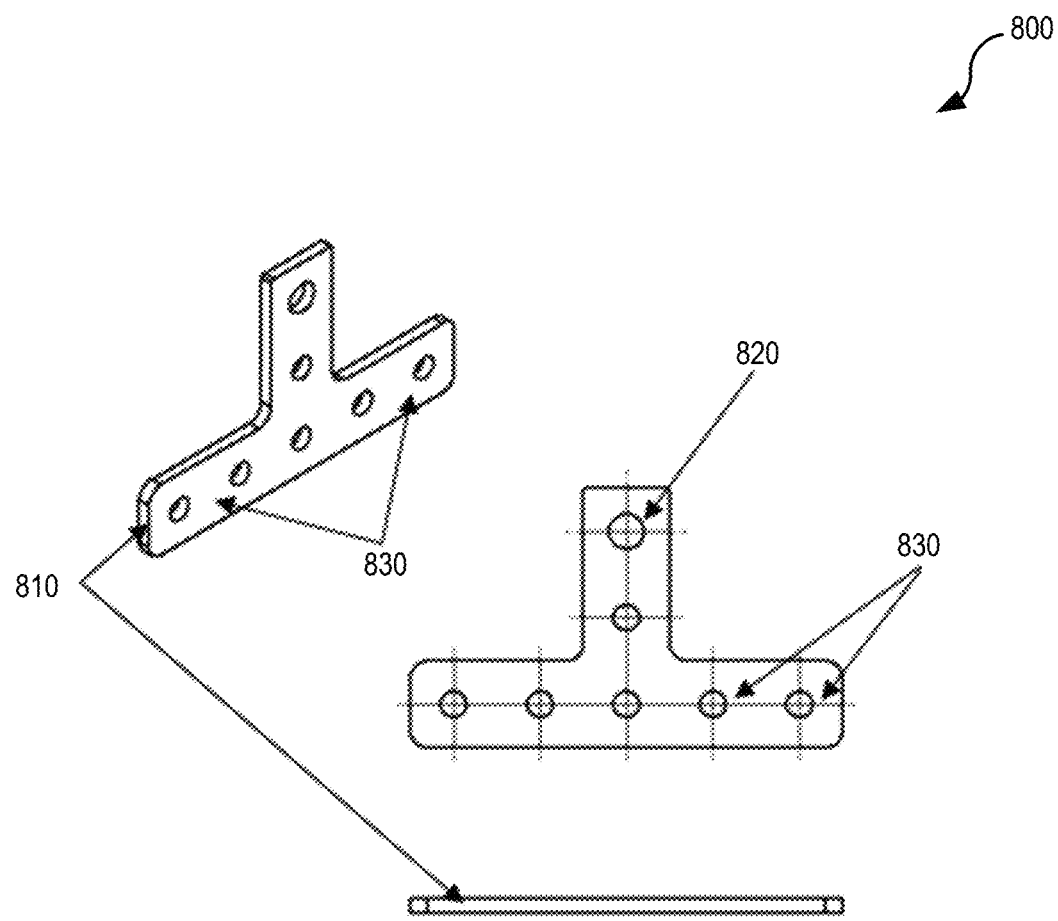
FIG. 8 illustrates an example of a mounting tab that may be used in accordance with various embodiments of the present technology.

FIG. 8 illustrates an example of a mounting tab 800 that may be used in accordance with various embodiments of the present technology. The mounting table can include a lateral member 810 and a transverse member (e.g., formed in a T-shape). In some embodiments, the lateral member 810 and the transverse member may include holes 830 which can be used to secure the mounting tab mounting bracket and/or prosthetic device. The transverse member 810 can be bent to conform to a prosthetic socket.

Figure 9:
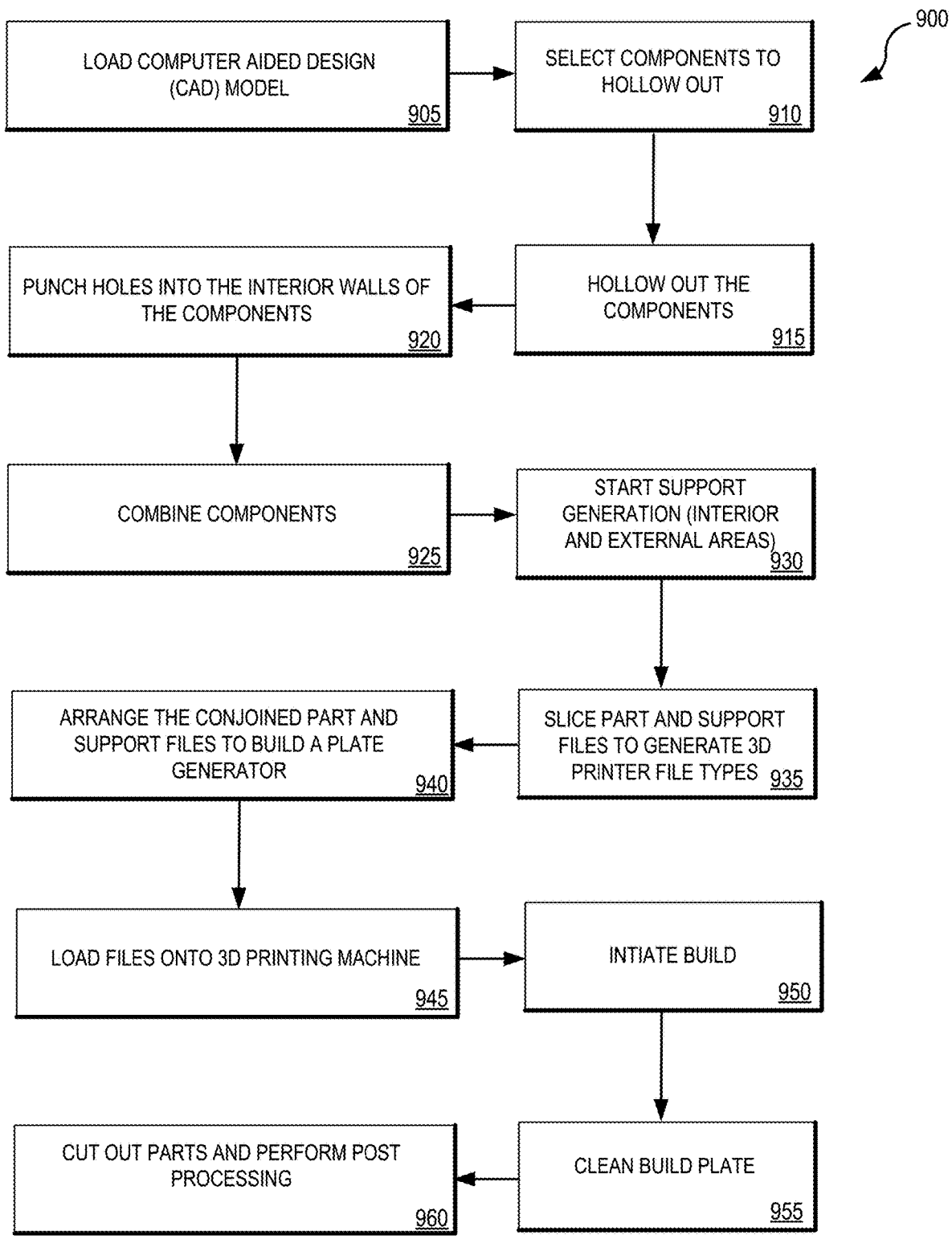
FIG. 9 illustrates an example of a set of operations for building a partial finger system in accordance with some embodiments of the present technology.

FIG. 9 illustrates an example of a set of operations 900 for building a prosthetic finger system in accordance with some embodiments of the present technology. In accordance with various embodiments, a computer aided design (e.g., a Solidworks generated STL model) can be loaded during operation 905 into computer design tool (e.g., Magics) for support generation. Any STL generation errors can be fixed and components can be selected to hollow out in operation 910. If the file has multiple components, the surfaces can be broken into individual parts. Then the component that will be hollowed can be selected. In some embodiments, the part can be hollowed in operation 915 so that the wall thickness reaches a desired thickness (e.g., 0.65 mm).

In some embodiments, holes can be punched into the interior walls of the component to allow for building powder evacuation during operation 920. The STL can be cleaned/fixed again, components can be combined and support generation can be started for the interior areas during operations 925 and 930. To minimize the amount of interior support, some embodiments can use blocks, gussets, or line supports. In some embodiments, the support may not have teeth but a solid connection with the part.

The parts can be arranged so key features are not covered in support. The part may be arranged so there is only enough support to keep the part in place during the build in various embodiments. The part and support files can be generated (e.g., by Magics) and then 'sliced' into an additive manufacturing file type (e.g., an EOS file type) during operation 935. The conjoined part and support files can be arranged on a build plate generator and the parts aligned for the best chance for a successful build during operation 940.

The file can be loaded onto the EOS machine during operation 945, and the build started using operation 950. The build chamber can be levelled and filled with Nitrogen gas so there is <1.3% Oxygen. In some embodiments, the build can take from 24 to 48 hours. Once the job is finished, the build plate can have the remaining powder sifted through and deposited in the dispenser hopper bin during operation 955. The powder from the collector bin can be sifted. Once the build plate is clean, it can be removed and placed on a jig for the bandsaw. Each of the parts can then be cut from the build plate during operation 960. During post processing, the in situ joints can be loosened, cutting wheels can be used to remove supports, peening surfaces can be shot, and deburring services can be applied.

Figure 10:
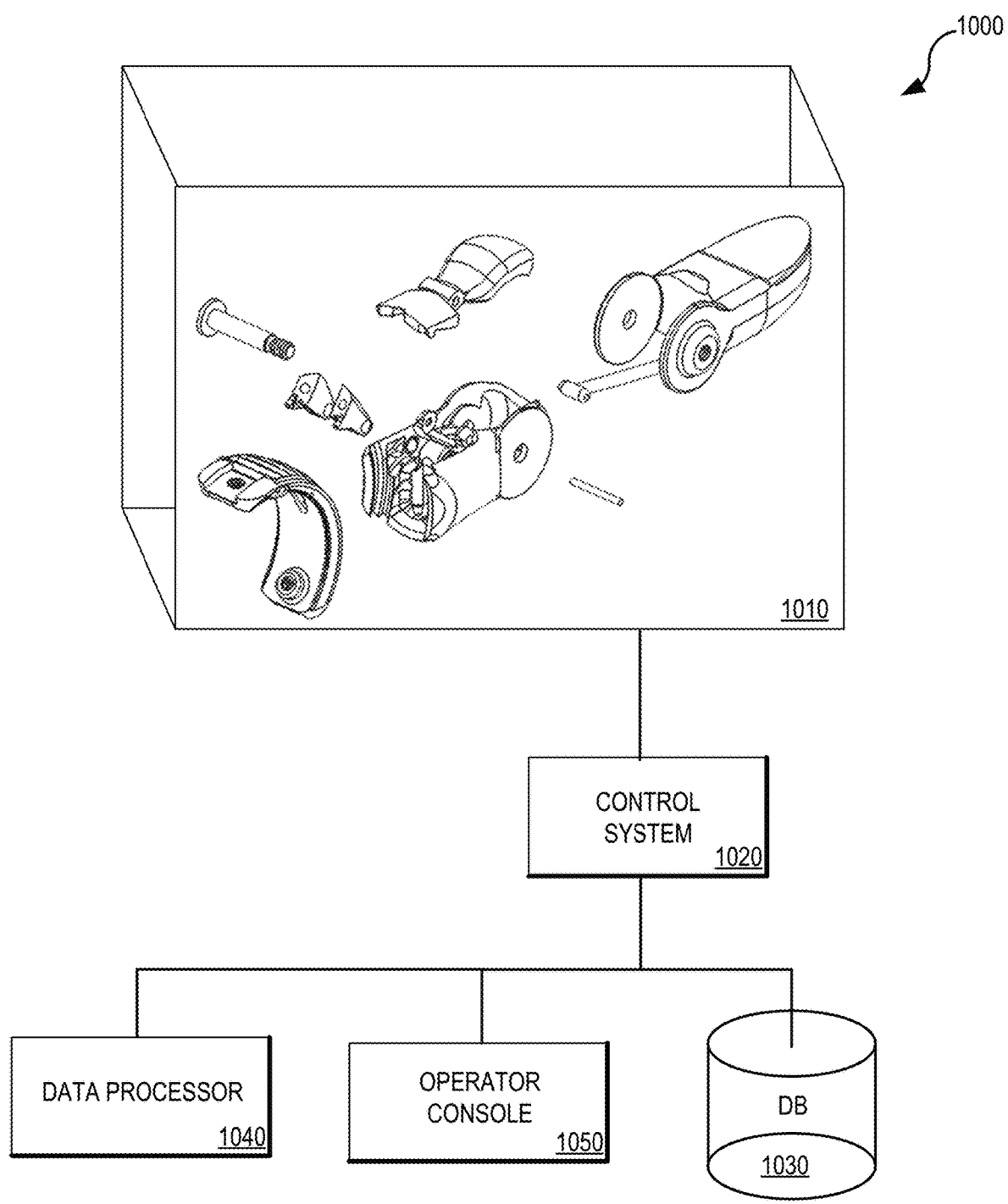
FIG. 10 illustrates an example of a set of components for a three-dimensional printing system that may be used in one or more embodiments of the present technology.

FIG. 10 illustrates an example of a set of components for a three-dimensional printing system that may be used in one or more embodiments of the present technology. In the embodiments illustrated in FIG. 10, three-dimensional printing system 1000 may include printer 1010, control system 1020, database 1030, data processor 1040, and operator console 1050. An operator can use operator console 1050 to command printer 1010 to create parts for one or more partial pivot designs. The control system 1020 can use computer-aided design files stored in database 1030 to control the printing process. In some embodiments, an operator can use operator console 1050 to select and control the design as well as review results.

Control system 1020 may be used in one or more embodiments of the present technology. Control system 1020 can include a communication interface for communicating with printer 1010 and operator console 1050. In accordance with various embodiments, control system 1020 can receive operator commands from operator console 1050, process those requests, and issue commands to printer 1010 indicating the manufacturing sequence. For example, the operator may take measurements from the user of the end device. Data processor 1040 can take those measurements and automatically scale the parts via a parameterization.

In accordance with various embodiments, the parameterization can be dictated by the golden ratio (or any other selected ratio). The length of the finger can be broken up into three phalanges, proximal, middle and distal. Since the design is for a partial finger, we eliminate the proximal phalange and design from the center of rotation of the PIP joint to the tip of the finger. All the subsequent features are lengthened to match the finger length, save any off the shelf components such as springs, pins and bolts. Range of motion remains constant. Knuckle diameter will also be parameterized.

$$\text{Golden Ratio: } \varphi = \frac{\sqrt{5}+1}{2} = 1.618\ldots$$

For the partial everything hinges on the intact hand's finger length L. Using the finger length, we can calculate the middle phalange length (M).

$$\varphi M + M + \frac{3M}{2\varphi} = L$$

$$M = \frac{L}{\varphi + 1 + \frac{3}{2\varphi}}$$

Distal Length (D) is calculated from the Middle length $$D = \frac{3M}{2\varphi}$$

Some embodiments can provide a fixed set of sized. For example, some embodiments may simply select between three sizes, 80 mm, 95 mm, 105 mm full finger equivalent.

| Full intact finger Lengths (mm) | Middle (mm) | Distal (mm) |
|---|---|---|
| 80 | 22.56645 | 20.92025 |
| 95 | 26.79767 | 24.8428 |
| 105 | 29.61847 | 27.45783 |
| Range of Motion | | |
| PIP | | DIP |
| 65° | | 50° |

In some embodiments, the geometry of the laser cut mounting bracket can provide optimal rigidity and ease of installation. The stiffness of the mounting bracket can be configured so that the bracket is bendable to conform around socket but rigid enough for adequate stability. The attachment orientation can be distal to knuckle track to enable lowest profile fitting possible.

Curved teeth on a spherical knuckle track can be used to improve the mechanical strength within space constraints. Some embodiments allow for more tooth face to improve mechanical strength within constrained width. A curved t-shaped connecting rod can be used to improve strength and prevents clashing with socket. In some embodiments, an integrated t-shape at proximal end can be used to improve strength. A curved t-shape can be used to fit constrained space and there may be no need for a pin.

The spherical knuckle track (e.g., curving in both dorsal/ventral and medial/lateral directions) can be used to enable closer conformal fitting to socket. In some embodiments, a curved prop and button can conform to spherical knuckle track. In some embodiments, multiple diameters of spherical shape to enable different sized residual limbs.

Advanced techniques can be used to reduce post-processing time and effort for DMLS manufacturing. For example, in some embodiments, holes can be used to release props from 3D printed supports for ease of post-processing. An extension tool may be used for dislodging props that fits into holes. Printed threads can be used to reduce componentry and reduce size and post-processing of digit. A support of linkages for tumbling may also be used.

Some embodiments use a parametrization of CAD file enables immediate custom sizing. Equations which relate finger length to dimensions within each component (e.g., props (×2), proximal phalange, distal phalange, lever, knuckle, connecting Rod, etc.). As such, 500+ dimensions can be automatically updated.

Some embodiments use a spherical knuckle track instead of cylindrical track. As a result, the parametrized diameter enables better fitting for different anatomy. The use of in-situ joints provides assembled printing which is robust to post-processing methods like tumbling and ease of assembly. Some embodiments created a union between distal and connecting rod. A prop can be removed in order to enable joint to move. The arrangement of the components in a vertical orientation can improve yield, evacuation of powder, reduces post-processing, preserves final geometry for majority of components. As a result, there can be a decrease support material amount, an improved evacuation of powder from components, a decrease in post-processing time, and/or, more final surfaces are exposed to final geometries.

Computer System

Figure 11:
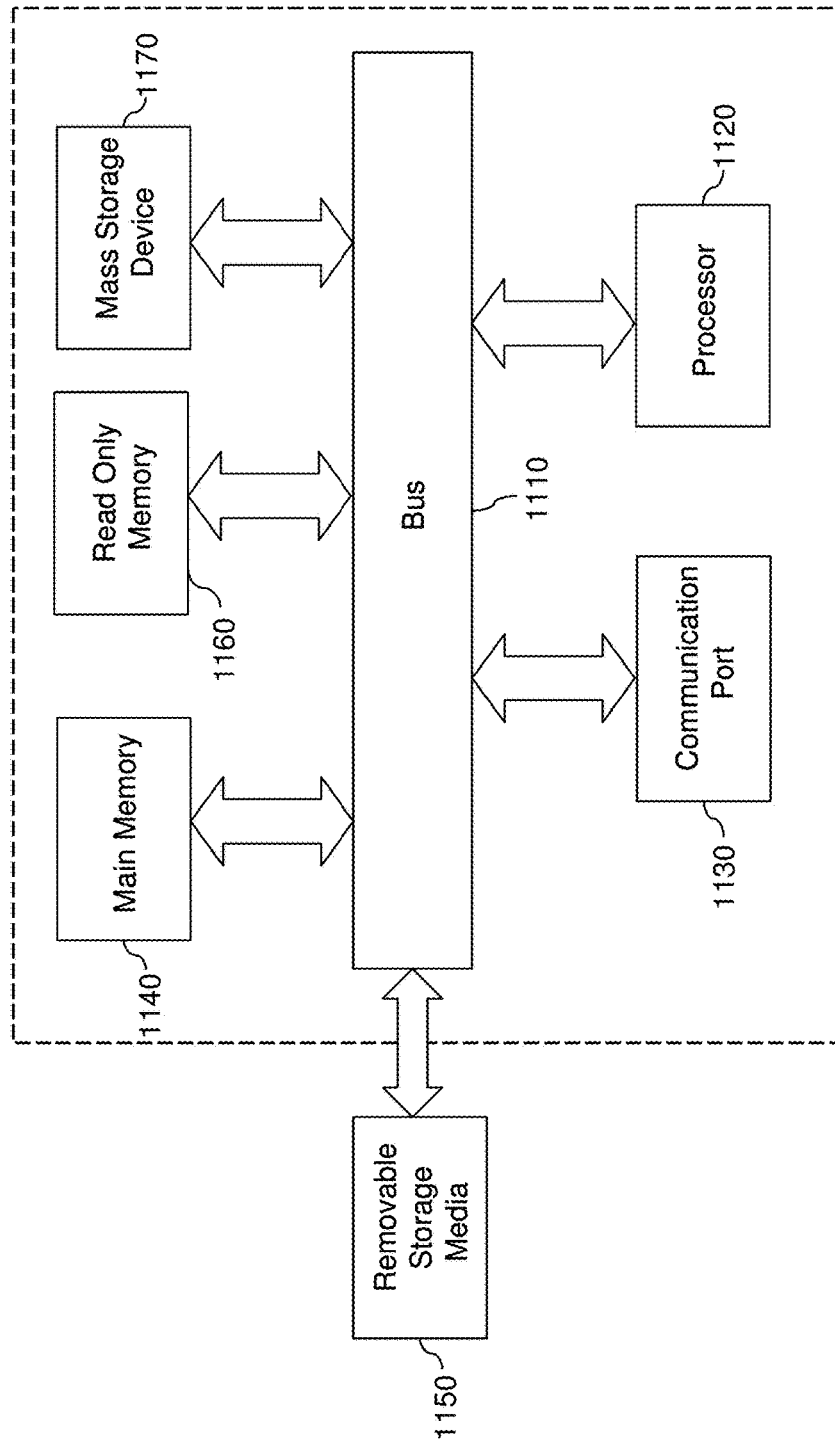
FIG. 11 is example of a computer system that may be used in accordance with various embodiments of the present technology.

Embodiments of the present invention include various steps and operations, which have been described above. A variety of these steps and operations may be performed by hardware components or may be embodied in machine-executable instructions, which may be used to cause a general-purpose or special-purpose processor programmed with the instructions to perform the steps. Alternatively, the steps may be performed by a combination of hardware, software, and/or firmware. As such, FIG. 11 is an example of a computer system 1100 with which embodiments of the present invention may be utilized. According to the present example, the computer system includes a bus 1110, at least one processor 1120, at least one communication port 1130, a main memory 1140, a removable storage media 1150, a read only memory 1160, and a mass storage 1170.

Processor(s) 1120 can be any known processor, such as, but not limited to, Intel® lines of processors; AMD® lines of processors; or Motorola® lines of processors. Communication port(s) 1130 can be any of an RS-232 port for use with a modem-based dialup connection, a 10/100 Ethernet port, or a Gigabit port using copper or fiber. Communication port(s) 1130 may be chosen depending on a network such as a Local Area Network (LAN), Wide Area Network (WAN), or any network to which the computer system 1100 connects.

Main memory 1140 can be Random Access Memory (RAM) or any other dynamic storage device(s) commonly known in the art. Read only memory 1160 can be any static storage device(s) such as Programmable Read Only Memory (PROM) chips for storing static information such as instructions for processor 1120.

Mass storage 1170 can be used to store information and instructions. For example, hard disks such as the Adaptec® family of SCSI drives, an optical disc, an array of disks such as RAID, such as the Adaptec family of RAID drives, or any other mass storage devices may be used.

Bus 1110 communicatively couples processor(s) 1120 with the other memory, storage and communication blocks. Bus 1110 can be a PCI/PCI-X or SCSI based system bus depending on the storage devices used.

Removable storage media 1150 can be any kind of external hard-drives, floppy drives, IOMEGA® Zip Drives, Compact Disc-Read Only Memory (CD-ROM), Compact Disc-Re-Writable (CD-RW), and/or Digital Video Disk-Read Only Memory (DVD-ROM), magnetic tape, flash drive, solid state memory, or the like.

The components described above are meant to exemplify some types of possibilities. In no way should the aforementioned examples limit the scope of the invention, as they are only exemplary embodiments.

Embodiments of the present invention may be implemented using a combination of one or more modules. For example, embodiments provide for a graphical user interface generation module to generation one or more graphical user interface screens to convey results/information and take instructions, a general-purpose or special-purpose "communications module" to receive and process various signals, as well as other modules for providing various functionality needed by embodiments of the present invention. Still yet, various embodiments may incorporate two or more of these modules into a single module and/or associate a portion of the functionality of one or more of these modules with a different module.

CONCLUSION

Unless the context clearly requires otherwise, throughout the description and the claims, the words "comprise," "comprising," and the like are to be construed in an inclusive sense, as opposed to an exclusive or exhaustive sense; that is to say, in the sense of "including, but not limited to." As used herein, the terms "connected," "coupled," or any variant thereof means any connection or coupling, either direct or indirect, between two or more elements; the coupling or connection between the elements can be physical, logical, or a combination thereof. Additionally, the words "herein," "above," "below," and words of similar import, when used in this application, refer to this application as a whole and not to any particular portions of this application. Where the context permits, words in the above Detailed Description using the singular or plural number may also include the plural or singular number respectively. The word "or," in reference to a list of two or more items, covers all of the following interpretations of the word: any of the items in the list, all of the items in the list, and any combination of the items in the list.

The above Detailed Description of examples of the technology is not intended to be exhaustive or to limit the technology to the precise form disclosed above. While specific examples for the technology are described above for illustrative purposes, various equivalent modifications are possible within the scope of the technology, as those skilled in the relevant art will recognize. For example, while processes or blocks are presented in a given order, alternative implementations may perform routines having steps, or employ systems having blocks, in a different order, and some processes or blocks may be deleted, moved, added, subdivided, combined, and/or modified to provide alternative or subcombinations. Each of these processes or blocks may be implemented in a variety of different ways. Also, while processes or blocks are at times shown as being performed in series, these processes or blocks may instead be performed or implemented in parallel, or may be performed at different times. Further any specific numbers noted herein are only examples: alternative implementations may employ differing values or ranges.

The teachings of the technology provided herein can be applied to other systems, not necessarily the system described above. The elements and acts of the various examples described above can be combined to provide further implementations of the technology. Some alternative implementations of the technology may include not only additional elements to those implementations noted above, but also may include fewer elements.

These and other changes can be made to the technology in light of the above Detailed Description. While the above description describes certain examples of the technology, and describes the best mode contemplated, no matter how detailed the above appears in text, the technology can be practiced in many ways. Details of the system may vary considerably in its specific implementation, while still being encompassed by the technology disclosed herein. As noted above, particular terminology used when describing certain features or aspects of the technology should not be taken to imply that the terminology is being redefined herein to be restricted to any specific characteristics, features, or aspects of the technology with which that terminology is associated. In general, the terms used in the following claims should not be construed to limit the technology to the specific examples disclosed in the specification, unless the above Detailed Description section explicitly defines such terms. Accordingly, the actual scope of the technology encompasses not only the disclosed examples, but also all equivalent ways of practicing or implementing the technology under the claims.

To reduce the number of claims, certain aspects of the technology are presented below in certain claim forms, but the applicant contemplates the various aspects of the technology in any number of claim forms. For example, while only one aspect of the technology is recited as a computer-readable medium claim, other aspects may likewise be embodied as a computer-readable medium claim, or in other forms, such as being embodied in a means-plus-function claim. Any claims intended to be treated under 35 U.S.C. § 112(f) will begin with the words "means for", but use of the term "for" in any other context is not intended to invoke treatment under 35 U.S.C. § 112(f). Accordingly, the applicant reserves the right to pursue additional claims after filing this application to pursue such additional claim forms, in either this application or in a continuing application.

What is claimed is:

1. A prosthetic device comprising:
   a partial finger consisting essentially of: a proximal phalange, and a distal phalange,
      wherein the distal phalange is directly coupled to the proximal phalange to create a joint allowing the distal phalange to move relative to the proximal phalange;
   a curved knuckle track coupled to the proximal phalange of the partial finger,
      wherein the curved knuckle track and the partial finger include a ratcheting mechanism to contact multiple teeth to allow movement in only a first direction relative to the curved knuckle track while the ratcheting mechanism is engaged; and
      wherein the curved knuckle track has one or more adjustable protruding stops that can be positioned along the curved knuckle track to set where full flexion of the partial finger occurs;
   a release button that, when engaged, disengages the ratcheting mechanism from the multiple teeth allowing an elastic restoring force to move the partial finger in a second direction relative to the knuckle track resulting in extension of the partial finger; and
   props that, when engaged by the one or more adjustable protruding stops, disengage the release button from the ratcheting mechanism allowing the elastic restoring force to move the partial finger in the second direction.

2. The prosthetic device of claim 1, further comprising a link bar connecting the distal phalange to the curved knuckle track, wherein the link bar causes the distal phalange to move relative to both the proximal phalange and the knuckle track as the proximal phalange moves relative to the knuckle track.

3. The prosthetic device of claim 1, wherein the elastic restoring force is created by a torsion spring located in the joint, wherein the torsion spring includes a first leg engaging the distal phalange and a second leg engaging the proximal phalange.

4. The prosthetic device of claim 1, wherein the curved knuckle track includes a channel on lateral edges of a first side to allow the props to engage.

5. The prosthetic device of claim 1, further comprising a mounting bracket that comprises:
   multiple metal lattice structures to create a foundation allowing socket material to adhere, wherein the multiple metal lattice structures are connected in an anatomical alignment via linking members;
   threaded mounting holes to affix the multiple metal lattice structure to the knuckle track using screws; and
   a mounting tab which can be conformed to a shape of a socket and provide additional structural support for the multiple metal lattice structures.

6. The prosthetic device of claim 1, wherein the partial finger is one of multiple partial fingers, and wherein the mounting bracket is configured to receive for attachment each of the multiple partial fingers so that flexion in one of the multiple partial fingers causes flexion across all other multiple partial fingers.

7. The prosthetic device of claim 6, wherein the flexion across all other multiple partial fingers varies in degree of flexion.

8. The prosthetic device of claim 1, wherein the knuckle track rounds in a lateral direction and a transverse direction relative to the multiple teeth so that the arc forms a sector of a sphere.

9. The prosthetic device of claim 8, wherein the multiple teeth are curved.

10. The prosthetic device of claim 1, wherein the proximal phalange and the distal phalange is shaped in a form of a thumb.

11. A prosthetic device comprising:
    a partial finger consisting essentially of: a proximal phalange, and a distal phalange hingedly coupled to the proximal phalange;
    a curved knuckle track coupled to the proximal phalange,
       wherein the curved knuckle track, the proximal phalange, and the distal phalange includes a ratcheting mechanism to contact multiple teeth to allow movement in only a first direction while the ratcheting mechanism is engaged;
    a release button that, when engaged, disengages the ratcheting mechanism from the multiple teeth allowing an elastic restoring force from a spring to move the partial finger in a second direction; and
    props that, when engaged upon the partial finger moving in the first direction to a full flexion position, disengages the release button from the ratcheting mechanism allowing the elastic restoring force to move the partial finger in the second direction.

12. The prosthetic device of claim 11, wherein the curved knuckle track has one or more protruding stops at a first end corresponding to full flexion of a finger created by the proximal phalange and the distal phalange.

13. The prosthetic device of claim 12, wherein the one or more protruding stops are moveable along the curved knuckle track resulting in a change in the full flexion of the partial finger created by the proximal phalange.

14. The prosthetic device of claim 11, wherein the proximal phalange reaches full flexion at the end of the curved knuckle track and activates a full flexion spring release point to disengage the ratcheting mechanism.

15. The prosthetic device of claim 11, wherein the knuckle track rounds in a lateral direction and a transverse direction relative to the multiple teeth so that the arc forms a sector of a sphere.

16. The prosthetic device of claim 15, wherein the multiple teeth are curved.

17. The prosthetic device of claim 11, wherein the proximal phalange and the distal phalange is shaped in a form of a thumb.

18. A device comprising:
    a partial finger consisting essentially of: a proximal phalange, and a distal phalange coupled to the proximal phalange;

a knuckle track formed in an arc and configured to be coupled to the proximal phalange,
    wherein the knuckle track includes multiple teeth formed on a first side on which the proximal phalange slides along,
    wherein the proximal phalange includes a ratcheting mechanism to contact the multiple teeth to allow sliding in only a first direction while the ratcheting mechanism is engaged; and
a release button configured to disengage the ratcheting mechanism from the multiple teeth to allow the distal phalange to slide in a second direction.

19. The device of claim 18, wherein the knuckle track rounds in a lateral direction and a transverse direction relative to the multiple teeth so that the arc forms a sector of a sphere.

20. The device of claim 19, wherein the multiple teeth are curved.

21. The device of claim 18, wherein there are least ten teeth on the knuckle track.

22. The device of claim 18, wherein the proximal phalange, the distal phalange, the knuckle track, and the release button are all printed using a three-dimensional printer.

23. The device of claim 22, wherein dimensions of the device are automatically scaled by a computer system based on a parameterized model of the device and wherein the computer system controls the three-dimensional printer to print the device in accordance with the dimensions.

24. The device of claim 18, further comprising a mounting bracket having one or more pliable extensions that can be bent to conform the mounting bracket to a socket configured to fit over a remaining portion of a finger and wherein the mounting bracket is securely affixed to a socket using one or more connecting mechanisms.

25. The device of claim 24, wherein the mounting bracket includes relief holes to promote bonding during lamination and exposed mounting holes for ease of attachment.

26. The device of claim 24, wherein the mounting bracket is detachable and comprises:
    multiple metal lattice structures to create a foundation allowing socket material to adhere, wherein the multiple metal lattice structures are connected in an anatomical alignment via linking members;
    threaded mounting holes to affix the multiple metal lattice structure to the knuckle track using screws; and
    a mounting tab which can be conformed to a shape of the socket and provide additional structural support for the multiple metal lattice structures.

27. The device of claim 18, wherein the device further comprises one or more props and wherein the proximal phalange and the one or more props are printed by a three-dimensional printer assembled with a live-hinge.

28. The device of claim 18, further comprising:
    A link chain having a proximal end and a distal end,
        wherein the proximal end is affixed to the knuckle track and the distal end is affixed to the distal phalange; and
        wherein the proximal phalange includes an opening through which the link chain is positioned causing the distal phalange to flex relative to the proximal phalange as the proximal phalange moves in the first direction.

29. The device of claim 18, further comprising a mounting track to provide a center of rotation about a physiological joint recreating physiological kinematics.

30. The device of claim 18, wherein the proximal phalange and the distal phalange is shaped in a form of a thumb.

\* \* \* \* \*